(12) United States Patent
Hook et al.

(10) Patent No.: US 8,586,802 B2
(45) Date of Patent: Nov. 19, 2013

(54) MULTI-STAGE PROCESS AND APPARATUS FOR RECOVERING DICHLOROHYDRINS

(75) Inventors: Bruce D. Hook, Lake Jackson, TX (US); Andrei Merenov, Lake Jackson, TX (US); Dan Tirtowidjojo, Lake Jackson, TX (US)

(73) Assignee: Dow Global Technologies LLC

( * ) Notice: Subject to any disclaimer, the term of this patent is extended or adjusted under 35 U.S.C. 154(b) by 493 days.

(21) Appl. No.: 12/935,303

(22) PCT Filed: Mar. 18, 2009

(86) PCT No.: PCT/US2009/037487
§ 371 (c)(1),
(2), (4) Date: Dec. 8, 2010

(87) PCT Pub. No.: WO2009/126415
PCT Pub. Date: Oct. 15, 2009

(65) Prior Publication Data
US 2011/0098516 A1    Apr. 28, 2011

Related U.S. Application Data

(60) Provisional application No. 61/043,590, filed on Apr. 9, 2008.

(51) Int. Cl.
 *C07C 29/78* (2006.01)
 *B01J 8/00* (2006.01)
(52) U.S. Cl.
 USPC .......................................... 568/913; 422/187
(58) Field of Classification Search
 USPC .......................... 568/913; 422/187
 See application file for complete search history.

(56) References Cited

FOREIGN PATENT DOCUMENTS

| | | |
|---|---|---|
| CN | 101007751 | 8/2007 |
| DE | 197308 | 4/1908 |
| EP | 1752435 | 2/2007 |
| EP | 1762556 | 3/2007 |
| WO | 2005021476 | 3/2005 |
| WO | 2005054167 | 6/2005 |
| WO | 2006020234 | 2/2006 |
| WO | 2008128004 | 10/2008 |

OTHER PUBLICATIONS

U.S. Appl. No. 60/923,108, filed Apr. 12, 2007, Tirtowidjojo et al.
U.S. Appl. No. 60/923,019, filed Apr. 12, 2007, Hook et al.
U.S. Appl. No. 60/923,055, filed Apr. 12, 2007, Briggs et al.

*Primary Examiner* — Sikarl Witherspoon

(57) ABSTRACT

A process and apparatus for recovering dichlorohydrins from a mixture comprising dichlorohydrins, one or more compounds selected from esters of dichlorohydrins, monochlorohydrins and/or esters thereof, and multihydroxylated-aliphatic hydrocarbon compounds and/or esters thereof, and optionally one or more substances comprising water, chlorinating agents, catalysts and/or esters of catalysts is disclosed. The mixture is distilled or fractionated to separate a lower boiling fraction comprising dichlorohydrin(s) from the mixture to form a higher boiling fraction comprising the residue of the distillation or fractionation. The higher boiling fraction is distilled or fractionated to separate remaining dichlorohydrin(s) from the above mixture to form an even higher boiling fraction comprising the residue of the distillation or fractionation. At least some of the lower boiling fraction and the dichlorohydrin(s) are recovered. Advantages include more efficient recovery of dichlorohydrins for a given distillation column, less waste due to avoiding the conditions conducive to the formation of heavy byproducts, reduced capital investment in recovery equipment, and reduced energy utilization while maintaining the quality of dichlorohydrin product produced and not increasing the amount of undesired byproducts formed.

16 Claims, 3 Drawing Sheets

MULTI-STAGE PROCESS AND APPARATUS FOR RECOVERING DICHLOROHYDRINS

CROSS REFERENCE TO RELATED APPLICATIONS

This is a §371 application of PCT International Patent Application Number PCT/US2009/037487 filed Mar. 18, 2009, and claims priority from provisional application Ser. No. 61/043,590 filed Apr. 9, 2008, which is incorporated herein by reference in its entirety.

BACKGROUND OF THE INVENTION

The present invention relates to processes and apparatus for recovering dichlorohydrins from a mixture comprising the same such as the effluent generated by a process for converting multihydroxylated-aliphatic hydrocarbon compound(s) and/or ester(s) thereof to chlorohydrins.

Dichlorohydrins are useful in preparing epoxides such as epichlorohydrin. Epichlorohydrin is a widely used precursor to epoxy resins. Epichlorohydrin is a monomer which is commonly used for the alkylation of para-bisphenol A. The resultant diepoxide, either as a free monomer or oligomeric diepoxide, may be advanced to high molecular weight resins which are used for example in electrical laminates, can coatings, automotive topcoats and clearcoats.

Glycerin is considered to be a low-cost, renewable feedstock that is a co-product of the biodiesel process for making fuel. It is known that other renewable feedstocks such as fructose, glucose and sorbitol can be hydrogenolized to produce mixtures of vicinal diols and triols, such as glycerin, ethylene glycol, 1,2-propylene glycol, 1,3-propylene glycol and the like. With abundant and low cost glycerin or mixed glycols, economically attractive processes for recovering dichlorohydrins from effluents produced by the above processes are desired.

A process is known for the conversion of glycerol (also referred to herein as "glycerin") to mixtures of dichloropropanols, compounds I and II, as shown in Scheme 1 below. The reaction is carried out in the presence of anhydrous HCl and an acetic acid (HOAc) catalyst with water removal. Compounds I and II can then be converted to epichlorohydrin via treatment with caustic or lime.

Scheme 1: Hydrochlorination of Glycerol

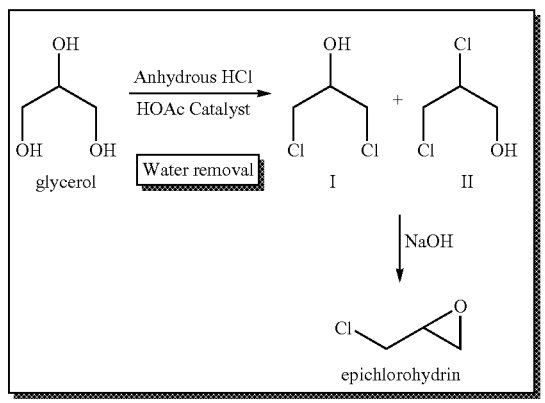

Various processes using the above chemistry in Scheme 1 have been reported in the prior art. For example, epichlorohydrin can be prepared by reacting a dichloropropanol such as 2,3-dichloro-1-propanol or 1,3-dichloro-2-propanol with base. Dichloropropanol, in turn, can be prepared at atmospheric pressure from glycerol, anhydrous hydrochloric acid, and an acid catalyst. A large excess of hydrogen chloride (HCl) was recommended to promote the azeotropic removal of water that is formed during the course of the reaction.

WO 2006/020234 A1 describes a process for conversion of a glycerol or an ester or a mixture thereof to a chlorohydrin, comprising the step of contacting a multihydroxylated-aliphatic hydrocarbon compound, an ester of a multihydroxylated-aliphatic hydrocarbon, or a mixture thereof with a source of a superatmospheric partial pressure of hydrogen chloride to produce chlorohydrins, esters of chlorohydrins, or mixtures thereof in the presence of an organic acid catalyst. This process is referred to herein as a "dry process" because the process uses dry hydrogen chloride and the source of water in the process is essentially only the water generated in the reaction as a co-product. In the dry process, azeotropic removal of water, via a large excess of hydrogen chloride, is not required to obtain high chlorohydrins yield. WO 2006/20234 A1 further teaches that separation of the product stream from the reaction mixture may be carried out with a suitable separation vessel such as one or more distillation columns, flash vessels, extraction columns or adsorption columns. WO 2006/020234 A1 does not describe a specific distillation process and apparatus for efficient recovery of dichlorohydrins or a method to minimize formation of heavy byproducts.

WO 2005/021476 A1 describes a process using atmospheric partial pressure of hydrogen chloride, acetic acid as the catalyst, and a cascade of loops, preferably three loops, each loop consisting of a reactor and a distillation column in which water of reaction, residual hydrogen chloride and dichloropropanol are removed from the reaction effluent. This process for distillation requiring a cascade of reactor/distillation loops is very expensive as it requires several reactors/columns loops in the process. WO 2005/021476 A1 also does not describe a specific distillation method or a method to minimize formation of heavy byproducts. Furthermore, valuable acetic acid is lost with the distillate during distillation, resulting in a large rate of acetic acid consumption in the process, making the process expensive to operate.

EP 1 752 435 A1 (also published as WO 2005/054167) as well as EP 1 762 556 A1 disclose other processes for producing chlorohydrins by reaction between glycerol and aqueous hydrogen chloride to produce dichlorohydrins, under atmospheric conditions. This process is referred to herein as a "wet process" as it, not only produces water from the reaction, but also adds a large amount of water into the process via the aqueous hydrogen chloride reactant. This wet process requires three separation columns, a distillation column for distillation of the reactor's gas phase to remove the large excess of water from the reaction medium while keeping hydrogen chloride in the process, a stripper column to strip water and hydrogen chloride from the reactor's liquid phase and yet another distillation or a stripping column for recovering dichloropropanol from the liquid phase exiting the stripper. Some dichloropropanol is removed from the reaction medium in the first and the second separation columns because of existence of a pseudoazeotrope among dichloropropanol, water and hydrogen chloride. The main fraction of dichloropropanol is collected from the top of the distillation or stripping column, third separation column. This process has a very high energy consumption because of the need to evaporate a large amount of water from the process. This process is unsuitable for efficiently recovering dichlorohydrins from a reaction effluent of a dry process. Similarly, adding substantial amounts of water to the dichloropropanol adds substantively to the wastewater treatment requirements of downstream operations.

CN 101007751A describes another process that combines wet and dry processes with two reactor in series, in which tubular reactor is used as the first reactor and foaming-tank reactor is used as the second reactor. Aqueous hydrogen chloride, glycerin, carboxylic acid catalyst are mixed and fed to the first reactor and gaseous hydrogen chloride is fed to the second reactor. Inert impurities are added to the gaseous hydrogen chloride feed in order to improve the efficiency of stripping water from the reaction mixture in the foaming-tank reactor. The azeotropic composition of generated water, dichloropropanol and hydrogen chloride and part of the catalyst are evaporated from the top of foaming-tank reactor. The liquid bottom product of the foaming-tank reactor enters to a rectifying tower for separation. The dichloropropanol product is obtained from the rectifying tower distillates and the tower bottom residue is recycled to the foaming-tank reactor. This process shows lower hydrogen chloride conversion than that of the dry process, generates excess water where azeotropic removal of water is required, which implies larger process equipment than that of the dry process. CN 101007751A also does not describe specific distillation method to minimize formation of heavy byproducts.

U.S. Provisional Patent Application Ser. No. 60/923,108 entitled "MULTI-STAGE PROCESS AND APPARATUS FOR RECOVERING DICHLOROHYDRINS" filed Apr. 12, 2007 by Tirtowidjojo et al. describes a dual column separation process for separating dichlorohydrins from the effluent streams of reactors, but uses a stripping agent to effect the evaporation of the dichlorohydrin (dichloropropanol) from the mixture. This stripping agent then requires subsequent separation unit operations to become sufficiently cleaned to either recycle as a stripping agent or to discharge to the environment. These subsequent separation unit operations are typically additional distillation/fractionation unit operations that significantly increase the energy utilization of the overall process.

Opportunities remain to further improve recovery of dichlorohydrins from a dichlorohydrins comprising stream, in a form that can be used in subsequent conversions, such as the conversion to epichlorohydrin, and reduce energy utilization while maintaining the quality of dichlorohydrin product produced and not increasing the amount of undesired byproducts formed.

SUMMARY OF THE INVENTION

One aspect of the present invention is a process for recovering dichlorohydrin(s) from a mixture comprising dichlorohydrin(s), one or more compounds selected from ester(s) of chlorohydrin(s), monochlorohydrin(s), and/or multihydroxylated-aliphatic hydrocarbon compound(s) and/or ester(s) thereof, and optionally one or more substances comprising water, chlorinating agent(s), catalyst(s), ester(s) of catalyst(s), and/or heavy byproduct(s), wherein the process comprises:

(a) providing a mixture comprising dichlorohydrin(s), one or more compounds selected from ester(s) of chlorohydrin(s), monochlorohydrin(s), and/or multihydroxylated-aliphatic hydrocarbon compound(s) and/or ester(s) thereof, and optionally one or more substances comprising water, chlorinating agent(s), catalyst(s), ester(s) of catalyst(s), and/or heavy byproduct(s);

(b) distilling or fractionating the mixture of step (a) in one or more unit operations to separate a lower boiling fraction comprising dichlorohydrin(s) and other lower boiling components present in the mixture from the mixture of step (a) to form a higher boiling fraction comprising the residue of the distillation or fractionating;

(c) distilling or fractionating the higher boiling fraction produced by step (b) in one or more unit operations to separate remaining dichlorohydrin(s) from the mixture of step (b) to form an even higher boiling fraction comprising the residue of the distillation or fractionation; and (d) recovering at least some of the lower boiling fraction of step (b) and the dichlorohydrin(s) of step (c).

Another aspect of the present invention is a method for producing dichlorohydrin(s), wherein the mixture provided in step (a) is produced or derived from hydrochlorination of monochlorohydrin(s) and/or ester(s) thereof and/or multihydroxylated-aliphatic hydrocarbon compound(s) and/or ester(s) thereof.

Yet another aspect of the present invention is an apparatus suitable for producing dichlorohydrin(s) from multihydroxylated-aliphatic hydrocarbon compound(s) and/or ester(s) thereof comprising:

(1) at least one reactor;

(2) at least one first separation device comprising at least one first liquid-vapor contacting device having a bottom end and a top end for applying a decreasing temperature gradient from the bottom end to the top end to substances within the first liquid-vapor contacting device; and (3) at least one second separation device comprising at least one second liquid-vapor contacting device having a bottom end and a top end for applying a decreasing temperature gradient from the bottom end to the top end to substances within the second liquid-vapor contacting device;

wherein the at least one reactor (10) is connected directly or indirectly to the at least one first separation device (20) for conducting a reactor effluent feed stream (13) from the at least one reactor (10) to the at least one first liquid-vapor contacting device of the at least one separation device (20) for distillation and/or fractionation, the at least one first separation device (20) is connected directly or indirectly to the at least one second separation device (30) for conducting a distilled or fractionated liquid residue feed stream (23) from the at least one first liquid-vapor contacting device of the at least one first separation device (20) to the at least one second liquid-vapor contacting device (30) for distillation and/or fractionation, the at least one first separation device (20) having a first port (21) for recovering a dichlorohydrin(s)-containing distillate, and the at least one second liquid-vapor contacting device (30) having at least one second port (31) for recovering a dichlorohydrin(s).

Yet a third aspect of the present invention is an apparatus suitable for producing dichlorohydrin(s) from multihydroxylated-aliphatic hydrocarbon compound(s) and/or ester(s) thereof comprising:

(1) at least one reactor;

(2) at least one first separation device comprising at least one first liquid-vapor contacting device having a bottom end and a top end for applying a decreasing temperature gradient from the bottom end to the top end to substances within the first liquid-vapor contacting device; and (3) at least one second separation device comprising at least one second liquid-vapor contacting device having a bottom end and a top end for applying a decreasing temperature gradient from the bottom end to the top end to substances within the second liquid-vapor contacting device, wherein the vapor stream leaving the at least one first separation device (20) enters the at least one second separation device (30) in the upper portion of the device, and a portion of the liquid flow from a lower portion of the second separating device (30) is returned to the at least one first separation device (20).

In one embodiment of the present invention, the liquid stream leaving the bottom end of separation device (20) may also enter the second separation device (30) in the lower portion of the second device (30).

In another embodiment of the present invention, effluent streams may exit the separation device (30) in at least three locations on the separation device (30) which may be for example a column: at least one above where the vapor from separation device (20) enters, at least one at the bottom end of the separation device (30) below where the liquid from separation device (20) enters, and at least one located on separation device (30) in between the entering locations of the streams feeding from separation device (20) to separation device (30).

In general, the surprising advantages of the present invention, in all of the different aspects of the present invention, comprise:

(a) the separation of the desired dichlorohydrin product from the chlorinating agent and the underconverted MAHC components is accomplished in a more energy efficient fashion than with a single large column or two columns of equivalent size (combined area) operated in parallel;

(b) less wastewater or vent gas requiring treatment is generated than when steam stripping or stripping with a non-condensable gas is used to drive evaporation in step (c) to lower the temperature at the base of the distillation column, while still maintaining sufficiently low reboiler temperatures that the formation of undesired byproducts is limited;

(c) allows a higher throughput by operating in series through two columns of maximum diameter due to materials of construction constraints than operating those same two columns in parallel;

(d) allows the columns to be operated at higher pressure, while maintaining the quality of the distilled product, therefore making large scale implementation of the process easier;

(e) removes the much more highly corrosive chlorinating agent and water in the first column, thereby allowing the second column to be made of a less corrosion resistant, and therefore lower cost, material; and (f) by pre-removing the water from the separation of most of the desired dichlorohydrin product, less pure grades of glycerin that contain higher water contents, such as so-called technical grade glycerin, may be used more economically in the hydrochlorination process.

Other additional advantages of the present invention may also comprise:

(1) a wider selection of vacuum devices and the ability to use of a more economical steam jet ejector, thereby reducing capital and operating costs;

(2) reduction of column size for a given feed volume due to the ability to operate at higher pressures, further reducing capital investment required; and (3) reduced heavy byproducts formation due to reduced distillation bottoms temperatures for increased product yield and reduced energy requirements for byproduct disposal.

DETAILED DESCRIPTION OF THE INVENTION

Definitions

Figure 1:
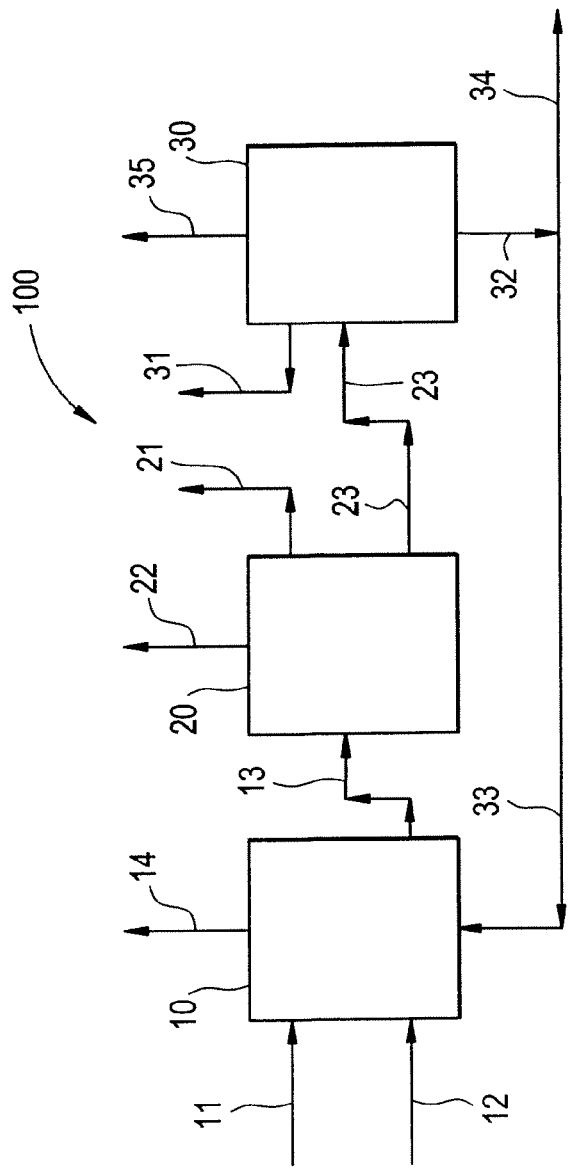
FIG. 1 is a process diagram illustrating one embodiment of the process of the present invention.

As used herein, the term "multihydroxylated-aliphatic hydrocarbon compound" (abbreviated hereafter as "MAHC") refers to a compound that contains at least two hydroxyl groups covalently bonded to two separate vicinal carbon atoms and no ether linking groups. They contain at least two sp3 hybridized carbons each bearing an OH group. The MAHCs include any vicinal-diol (1,2-diol) or triol (1,2,3-triol) containing hydrocarbon including higher orders of contiguous or vicinal repeat units. The definition of MAHC also includes for example one or more 1,3- 1,4-, 1,5- and 1,6-diol functional groups as well. Geminal-diols, for example, are precluded from this class of MAHCs.

The MAHCs contain at least about 2, preferably at least about 3, up to about 60, preferably up to about 20, more preferably up to about 10, even more preferably up to about 4, and yet more preferably up to about 3, carbon atoms and can contain, in addition to aliphatic hydrocarbon, aromatic moieties or heteroatoms including for example halide, sulfur, phosphorus, nitrogen, oxygen, silicon, and boron heteroatoms; and mixtures thereof. The MAHCs may also be a polymer such as polyvinyl alcohol.

The terms "glycerin", "glycerol" and "glycerine", and esters thereof, may be used as synonyms for the compound 1,2,3-trihydroxypropane, and esters thereof.

As used herein, the term "chlorohydrin" means a compound containing at least one hydroxyl group and at least one chlorine atom covalently bonded to two separate vicinal aliphatic carbon atoms and no ether linking groups. Chlorohydrins are obtainable by replacing one or more hydroxyl groups of MAHCs with covalently bonded chlorine atoms via hydrochlorination. The chlorohydrins contain at least about 2, and preferably at least about 3, up to about 60, preferably up to about 20, more preferably up to about 10, even more preferably up to about 4, and yet more preferably up to about 3, carbon atoms and, in addition to aliphatic hydrocarbon, can contain aromatic moieties or heteroatoms including for example halide, sulfur, phosphorus, nitrogen, oxygen, silicon, and boron heteroatoms, and mixtures thereof. A chlorohydrin that contains at least two hydroxyl groups is also a MAHC.

As used herein, the term "monochlorohydrin" means chlorohydrin having one chlorine atom and at least two hydroxyl groups, wherein the chlorine atom and at least one hydroxyl group are covalently bonded to two separate vicinal aliphatic carbon atoms (referred to hereafter by the abbreviation "MCH"). MCH produced by hydrochlorination of glycerin or glycerin esters includes, for example, 3-chloro-1,2-propanediol and 2-chloro-1,3-propanediol.

As used herein, the term "dichlorohydrin" means chlorohydrin having two chlorine atoms and at least one hydroxyl group, wherein at least one chlorine atom and at least one hydroxyl group are covalently bonded to two separate vicinal aliphatic carbon atoms (referred to hereafter by the abbreviation "DCH"). Dichlorohydrins produced by hydrochlorination of glycerin or glycerin esters include 1,3-dichloro-2-propanol and 2,3-dichloro-1-propanol.

As used herein, the expression "under hydrochlorination conditions" means conditions capable of converting at least about 1 wt. %, preferably at least about 5 wt. %, more preferably at least about 10 wt. % of MAHCs, MCHs, and esters of MAHCs and MCHs present in a mixture and/or feed stream into DCH(s) and/or ester(s) thereof.

As used herein, the term "byproduct(s)" means compound(s) that is/are not chlorohydrin(s) and/or ester(s) thereof and/or chlorinating agent(s) and that do not form chlorohydrin(s) and/or ester(s) thereof under the hydrochlorinating conditions selected according to the present invention.

The expression "heavy byproduct(s)" refer to oligomers of mixture (a) components, such as oligomers of MAHCs and/or esters thereof and oligomers of chlorohydrins and/or esters thereof, and derivatives of such oligomers, such as esters thereof, chlorinated oligomers, and/or chlorinated esters thereof, having a number average molecular weight equal to or greater than the number average molecular weight of the oligomer, such as chlorinated oligomers. The terms chlorohydrin(s), MCH(s) and DCH(s), and ester(s) thereof, are not intended to include heavy byproducts.

The term "epoxide" means a compound containing at least one oxygen bridge on a carbon-carbon bond. Generally, the carbon atoms of the carbon-carbon bond are contiguous and the compound can include other atoms than carbon and oxygen atoms, like hydrogen and halogens, for example. Preferred epoxides are ethylene oxide, propylene oxide, glycidol and epichlorohydrin.

As used herein, the expression, "liquid phase" refers to a continuous intermediate phase between gas phase and a solid phase that may optionally comprise a minor amount of gas and/or solid discrete phase(s). The liquid phase may comprise one or more immiscible liquid phases and may contain one or more dissolved solids, such as one or more acids, bases, or salts.

As used herein, the expression "vapor phase" refers to a continuous gaseous phase that may optionally comprise a minor amount of liquid and/or solid discrete phase(s) (e.g., aerosol). The vapor phase may be a single gas or a mixture, such as a mixture of two or more gases, two or more liquid discrete phases, and/or two or more solid discrete phases.

The expression "lower boiling fraction" refers to a fraction derived from the mixture provided in step (a) in which more than half the total quantity of components of the lower boiling fraction are components of the mixture, or derived from the mixture, that are more volatile under the conditions of the unit operation than the components of the higher boiling fraction in the same unit operation derived from the same mixture provided in step (a).

The expression "higher boiling fraction" refers to a fraction derived from the mixture provided in step (a) in which more than half the total quantity of components of the higher boiling fraction are components of the mixture, or derived from the mixture, that are less volatile than the components of the lower boiling fraction in the same unit operation derived from the same mixture provided in step (a).

As used herein, the expression "liquid-vapor contacting device" refers to devices that serve to provide the contacting and development of at least one interfacial surface between liquid and vapor in the device. Examples of liquid-vapor contacting devices include plate column, packed column, wetted-wall (falling film) column, spray chamber, heat exchanger or any combination thereof. Examples of devices comprising plate columns and packed columns include distillation columns, fractionation columns, and stripping columns.

As used herein, the term "condenser" means a non-adiabatic system for removing heat from a process fluid via a secondary fluid physically separated from the process fluid. The process fluid and the secondary fluid may each be a vapor, a liquid, or a combination of liquid and vapor. A condenser is generally associated with a section of a distillation or fractionation column. It may be a unit operation external to a distillation column or it may be a unit operation internal to a distillation column. The physical separation may be in the form of tubes and the condensation may be carried out on the inside or outside of the tubes. The condenser may take the faun of cooling elements on the decks of distillation column fractionating trays or as cooling elements between distillation column packing beds.

Mixture (a):

Mixture (a) may be obtained directly or indirectly from any hydrochlorination process well-known in the art. For example, German Patent No. 197308 teaches a process for preparing a chlorohydrin by the catalytic hydrochlorination of glycerin by means of anhydrous hydrogen chloride. WO 2005/021476 discloses a continuous process for preparing the dichloropropanols by hydrochlorination of glycerin and/or monochloropropanediols with gaseous hydrogen chloride with catalysis of a carboxylic acid. WO 2006/020234 A1 describes a process for conversion of a glycerol or an ester or a mixture thereof to a chlorohydrin, comprising the step of contacting a MAHC, an ester of a MAHC, or a mixture thereof with a source of a superatmospheric partial pressure of hydrogen chloride to produce a chlorohydrin, an ester of a chlorohydrin, or a mixture thereof in the presence of an organic acid catalyst without substantially removing water. The above references are hereby incorporated herein by reference with respect to the above-described disclosures.

In an exemplifying hydrochlorination process, MAHC and a hydrochlorination catalyst are charged to the hydrochlorination reactor. Then a chlorinating agent such as hydrogen chloride is added to the reactor. The reactor pressure is adjusted to the desired pressure and the reactor contents are heated to the desired temperature for the desired length of time. After completion of the hydrochlorination reaction or while carrying out the hydrochlorination reaction, the reactor contents as a reaction effluent stream is discharged from the reactor and fed directly, or indirectly via another reactor or other intervening step, to a separation system comprising a DCH recovery system according to the present invention and optionally including other separation systems or equipment, such as a flash vessel and/or reboiler.

The hydrochlorination reaction above may be carried out in one or more hydrochlorination reactor vessels such as a single or multiple continuous stirred tank reactors (referred to hereafter by the abbreviation "CSTR"), single or multiple tubular reactor(s), plug flow reactors (referred to hereafter by the abbreviation "PFR"), or combinations thereof. The hydrochlorination reactor can be, for example, one reactor or multiple reactors connected with each other in series or in parallel including, for example, one or more CSTRs, one or more tubular reactors, one or more PFRs, one or more bubble column reactors, and combinations thereof.

In a preferred embodiment, part or all of the hydrochlorination effluent stream is a feed stream from a PFR. A PFR is a type of reactor that has a high length/diameter (L/D) ratio and has a composition profile along the length of the reactor. The concentration of the reactants being fed into the PFR decreases from inlet to the outlet along the flow path of the PFR and the concentration of DCHs increases from inlet to the outlet along the flow path of the PFR. In the case of hydrochlorination of glycerol, the concentration of HCl and glycerol decreases from inlet of the PFR to outlet of the PFR while the total concentration of 1,3-dichloro-2-propanol and 2,3-dichloro-1-propanol increases from inlet of the PFR to the outlet of the PFR.

The equipment useful for conducting the hydrochlorination reaction may be any well-known equipment in the art and should be capable of containing the reaction mixture at the conditions of the hydrochlorination. Suitable equipment may be fabricated of materials which are resistant to corrosion by the process components, and may include for example, metals such as tantalum, suitable metallic alloys (particularly nickel-molybdenum alloys such as Hastelloy C™), or glass-lined equipment, for example.

In addition to DCH(s), one or more of the unreacted MAHC(s) and/or chlorination agent(s), reaction intermediates such as MCH(s), MCH ester(s), and/or DCH ester(s), catalyst(s), ester(s) of catalyst(s), water, and/or heavy byproduct(s) may present in mixture (a). A recycle process is preferred in which one or more of the unreacted MAHC(s), ester(s) of MAHC(s) and/or chlorination agent(s), reaction intermediates such as MCH(s), MCH ester(s), DCH ester(s), and other substances such as catalyst(s), ester(s) of catalyst(s), and water are preferably recycled to a prior step in the process, such as to at least one hydrochlorination reactor for further hydrochlorination. In particular, a liquid higher boiling fraction comprising a residue of the stripping step containing one or more of MAHC(s), MCH(s), catalyst(s), and/or ester(s) of one or more MAHC(s), MCH(s), DCH(s) and/or catalyst(s), and preferably a combination of two or more thereof, is recycled to the hydrochlorination step, such as by recycling the higher boiling fraction to one or more reactor(s). Such recycle process(es) is preferably continuous. In this manner, raw material efficiencies are maximized and/or catalysts are reused.

When catalysts are reused in such a process scheme, it may be desirable to employ the catalysts in a higher concentration than they are employed in a single-pass process. This may result in faster reactions, or smaller process equipment, which results in lower capital costs for the equipment employed.

In a continuous recycle process, undesirable impurities and/or reaction byproducts may build up in the process. Thus, it is desirable to provide a means for removing such impurities from the process, such as via one or more purge outlets, for example, or by a separation step. Furthermore, a purged stream may be further treated to recover a useful portion of the purged stream.

The chlorinating agent that may optionally be present in the mixture treated according to the present invention is preferably hydrogen chloride or hydrogen chloride source, and may be a gas, a liquid or in a solution, or a mixture thereof. The hydrogen chloride is preferably introduced in the gaseous state and, when the hydrochlorination reaction mixture is in the liquid phase, at least some of the hydrogen chloride gas is preferably dissolved in the liquid reaction mixture. The hydrogen chloride may, however, be diluted in a solvent, such as an alcohol (for example methanol) or a chlorinated hydrocarbon, or in a carrier gas such as nitrogen, if desired.

In one embodiment of the present invention, the hydrochlorination step of the present invention may be carried out under superatmospheric pressure conditions, although the present invention is not limited thereto, viz, the hydrochlorination step of the present invention may be carried out under sub-atmospheric, atmospheric and superatmospheric pressure conditions. "Superatmospheric pressure" herein means that the hydrogen chloride (HCl) partial pressure is above atmospheric pressure, i.e. about 15 psia (103 kPa) or greater. Generally, in a preferred embodiment, the hydrogen chloride partial pressure employed in the hydrochlorination process is at least about 15 psia (103 kPa) or greater. Preferably, the hydrogen chloride partial pressure employed in the hydrochlorination process is not less than about 25 psia (172 kPa), more preferably not less than about 35 psia (241 kPa), and most preferably not less than about 55 psia (379 kPa); and preferably not greater than about 1000 psia (6.9 MPa), more preferably not greater than about 600 psia (4.1 MPa), and most preferably not greater than about 150 psia (1.0 MPa).

It is also preferred to conduct the hydrochlorination step at a temperature sufficient for hydrochlorination that is also below the boiling point of the chlorohydrin(s) in the reaction mixture having the lowest boiling point for a given pressure condition during the hydrochlorination step in order to keep the chlorohydrin(s) produced and converted during hydrochlorination in the liquid phase of the reaction mixture for recovery in steps (b) and (c). The upper limit of this preferred temperature range may be adjusted by adjusting the pressure condition. A higher pressure during hydrochlorination may be selected to increase the boiling point temperature of the chlorohydrin(s) in the reaction mixture, so that the preferred temperature range for keeping DCH(s) in the liquid phase may be increased by increasing the pressure condition.

Preferably, less than about 50, more preferably less than about 10, even more preferably less than about 5, and yet more preferably less than about 1, percent of the DCH present in the hydrochlorination effluent is removed from the hydrochlorination effluent prior to step (b).

The hydrochlorination effluent comprises one or more DCHs, one or more compounds comprising ester(s) of DCH(s), MCH(s) and/or ester(s) thereof, and MAHC(s) and/or ester(s) thereof, and optionally one or more substances comprising water, chlorination agent(s), catalyst(s) and/or ester(s) of catalyst(s). Additional optional components may also be present in the effluent depending on the starting materials, reaction conditions, and any process steps intervening between the hydrochlorination reaction and recovery of DCH according to the present invention. The hydrochlorination effluent is preferably in the liquid phase as the hydrochlorination effluent is withdrawn from the hydrochlorination step and/or reactor and the mixture provided in step (a) comprises at least part of the liquid phase effluent of the hydrochlorination step.

In a preferred embodiment, at least one MAHC and/or ester thereof is present in the mixture provided in step (a). When MAHC(s) and/or ester(s) thereof is/are present in the mixture provided in step (a), the same MAHC(s) and/or ester(s) thereof may also be present in the high-boiling fraction of step (b).

MAHCs found in the effluent treated according the present invention may include for example 1,2-ethanediol; 1,2-propanediol; 1,3-propanediol; 3-chloro-1,2-propanediol; 2-chloro-1,3-propanediol; 1,4-butanediol; 1,5-pentanediol; cyclohexanediols; 1,2-butanediol; 1,2-cyclohexanedimethanol; 1,2,3-propanetriol (also known as, and used herein interchangeable as, "glycerin", "glycerine", or "glycerol"); and mixtures thereof. Preferably, the MAHCs in the effluents treated according to the present invention include for example 1,2-ethanediol; 1,2-propanediol; 1,3-propanediol; and 1,2,3-propanetriol; with 1,2,3-propanetriol being most preferred.

Examples of esters of MAHCs found in the effluents treated according to the present invention include for example ethylene glycol monoacetate, propanediol monoacetates, glycerin monoacetates, glycerin monostearates, glycerin diacetates, and mixtures thereof. In one embodiment, such esters can be made from mixtures of MAHC with exhaustively esterified MAHC, for example mixtures of glycerol triacetate and glycerol.

In the same or another preferred embodiment, at least one MCH and/or ester thereof is present in the mixture provided in step (a). When MCH(s) and/or ester(s) thereof is/are present in the mixture provided in step (a), the same MCH(s) and/or ester(s) thereof may also be present in the high-boiling fraction of step (b).

The MCHs generally correspond to the hydrochlorinated MAHCs in which one of a pair of hydroxyl groups covalently bonded to two separate vicinal carbon atoms is replaced by a covalently bonded chlorine atom. The ester(s) of MCH may be the result of hydrochlorination of MAHC ester(s) or reaction with an acid catalyst, for example.

The DCHs generally correspond to the hydrochlorinated MAHCs in which two hydroxyl groups covalently bonded to two separate carbon atoms, at least one of which is vicinal to a third carbon atom having a hydroxyl group, are each replaced by a covalently bonded chlorine atom. The ester(s) of DCH may be the result of hydrochlorination of MAHC ester(s), MCH ester(s) or reaction(s) with acid catalyst(s), for example.

In an embodiment of the present invention where MAHC(s) is/are the starting material fed to the process, as opposed to ester(s) of MAHC(s) or a mixture of MAHC(s) and ester(s) thereof as a starting material, it is generally preferred that the formation of chlorohydrin be promoted by the presence of one or more catalyst(s) and/or ester(s) thereof. Catalyst(s) and/or ester(s) thereof may also be present where ester(s) of MAHC(s), or a mixture of MAHC(s) and ester(s) thereof, is a starting material to further accelerate the hydrochlorination reaction.

Carboxylic acids, RCOOH, catalyze the hydrochlorination of MAHCs to chlorohydrins. The specific carboxylic acid catalyst chosen may be based upon a number of factors including for example, its efficacy as a catalyst, its cost, its stability to reaction conditions, and its physical properties. The particular process, and process scheme in which the catalyst is to be employed may also be a factor in selecting the particular catalyst. The "R" groups of the carboxylic acid may be independently chosen from hydrogen or hydrocarbyl groups, including alkyl, aryl, aralkyl, and alkaryl. The hydrocarbyl groups may be linear, branched or cyclic, and may be substituted or un-substituted. Permissible substituents include any functional group that does not detrimentally interfere with the performance of the catalyst, and may include heteroatoms. Non-limiting examples of permissible functional groups include chloride, bromide, iodide, hydroxyl, phenol, ether, amide, primary amine, secondary amine, tertiary amine, quaternary ammonium, sulfonate, sulfonic acid, phosphonate, and phosphonic acid.

The carboxylic acids useful as hydrochlorination catalysts may be monobasic such as acetic acid, formic acid, propionic acid, butyric acid, isobutyric acid, hexanoic acid, 4-methylvaleric acid, heptanoic acid, oleic acid, or stearic acid; or polybasic such as succinic acid, adipic acid, or terephthalic acid. Examples of aralkyl carboxylic acids include phenylacetic acid and 4-aminophenylacetic acid. Examples of substituted carboxylic acids include 4-aminobutyric acid, 4-dimethylaminobutyric acid, 6-aminocaproic acid, 6-hydroxyhexanoic acid, 6-chlorohexanoic acid, 6-aminohexanoic acid, 4-aminophenylacetic acid, 4-hydroxyphenylacetic acid, lactic acid, glycolic acid, 4-dimethylaminobutyric acid, and 4-trimethylammoniumbutyric acid. Additionally, materials that can be converted into carboxylic acids under reaction conditions, including for example carboxylic acid halides, such as acetyl chloride, 6-chlorohexanoyl chloride, 6-hydroxyhexanoyl chloride, 6-hydroxyhexanoic acid, and 4-trimethylammonium butyric acid chloride; carboxylic acid anhydrides such as acetic anhydride and maleic anhydride; carboxylic acid esters such as methyl acetate, methyl propionate, methyl pivalate, methyl butyrate, ethylene glycol monoacetate, ethylene glycol diacetate, propanediol monoacetates, propanediol diacetates, glycerin monoacetates, glycerin diacetates, glycerin triacetate, and glycerin esters of a carboxylic acid (including glycerin mono-, di-, and tri-esters); MAHC acetates such as glycerol 1,2-diacetate; carboxylic acid amides such as ε-caprolactam and γ-butyrolactam; and carboxylic acid lactones such as γ-butyrolactone, δ-valerolactone and ε-caprolactone may also be employed in the present invention. Zinc acetate is an example of a metal organic compound. Mixtures of the foregoing catalysts and catalyst precursors may also be used.

When a catalyst is used in the superatmospheric pressure process, the catalyst may be for example a carboxylic acid; an anhydride; an acid chloride; an ester; a lactone; a lactam; an amide; a metal organic compound such as sodium acetate; or a combination thereof. Any compound that is convertible to a carboxylic acid or a functionalized carboxylic acid under hydrochlorination reaction conditions may also be used. A preferred carboxylic acid for the superatmospheric pressure process is an acid with a functional group consisting of a halogen, an amine, an alcohol, an alkylated amine, a sulfhydryl, an aryl group or an alkyl group, or combinations thereof, wherein this moiety does not sterically hinder the carboxylic acid group.

Certain catalysts may also be advantageously employed at superatmospheric, atmospheric or sub-atmospheric pressure, and particularly in circumstances where water is continuously or periodically removed from the reaction mixture to drive conversion to desirably higher levels as may be the case when recovering DCH(s) according to the claimed invention. For example, the hydrochlorination of MAHC(s) reaction can be practiced by introducing hydrogen chloride gas into contact with a mixture of MAHC(s) and catalyst(s), such as by sparging the hydrogen chloride gas through a liquid phase reaction mixture. In such a process, the use of less volatile catalysts, such as 6-hydroxyhexanoic acid, 4-aminobutyric acid; dimethyl 4-aminobutyric acid; 6-chlorohexanoic acid; caprolactone; carboxylic acid amides such as ε-caprolactam and γ-butyrolactam; carboxylic acid lactones such as γ-butyrolactone, δ-valerolactone and ε-caprolactone; caprolactam; 4-hydroxyphenyl acetic acid; 6-amino-caproic acid; 4-aminophenylacetic acid; lactic acid; glycolic acid; 4-dimethylamino-butyric acid; 4-trimethylammoniumbutyric acid; and combination thereof; and the like may be preferred. It is most desirable to employ a catalyst, under these atmospheric or subatmospheric conditions, that is less volatile than the DCH(s) produced and recovered.

Preferred catalysts used in the present invention include carboxylic acids, esters of carboxylic acids, and combinations thereof, particularly esters and acids having a boiling point higher than that of the desired highest boiling DCH that is formed in the reaction mixture (i.e., the catalyst(s) is/are preferably less volatile than the DCH(s) in the mixture), so that the DCH(s) can be removed without removing the catalyst. Catalysts which meet this definition and are useful in the present invention include for example, polyacrylic acid, glycerin esters of carboxylic acids (including glycerin mono-, di-, and tri-esters), polyethylene grafted with acrylic acid, divinylbenzene/methacrylic acid copolymer, 6-chlorohexanoic acid, 4-chlorobutanoic acid, caprolactone, heptanoic acid, 4-hydroxyphenylacetic acid, 4-aminophenylacetic acid, 6-hydroxyhexanoic acid, 4-aminobutyric acid, 4-dimethylaminobutyric acid, 4-trimethyl-ammoniumbutyric acid chloride, stearic acid, 5-chlorovaleric acid, 6-hydroxyhexanoic acid, 4-aminophenylacetic acid, and mixtures thereof. Carboxylic acids that are sterically unencumbered around the carboxylic acid group are generally preferred.

Furthermore, the catalyst(s) is/are preferably miscible with the MAHC(s) employed. For this reason, the catalyst(s) may contain polar heteroatom substituents such as hydroxyl, amino or substituted amino, or halide groups, which render the catalyst miscible with the MAHC(s) in the reaction mixture, such as glycerol.

One embodiment of the catalyst that may be present is generally represented by Formula (a) shown below wherein the functional group "R'" includes a functional group comprising an amine, an alcohol, a halogen, a sulfhydryl, an ether; or an alkyl, an aryl or alkaryl group of from 1 to about 20 carbon atoms containing said functional group; or a combination thereof; and wherein the functional group "R" may include a hydrogen, an alkali, an alkali earth or a transition metal or a hydrocarbon functional group.

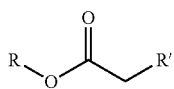

Formula (a)

Where the catalyst is recycled and used repeatedly, such recycled catalysts may be present in an amount from about 0.1 mole %, preferably from about 1 mole %, more preferably from about 5 mole %, up to about 99.9 mole %, preferably up to about 70 mol %, and more preferably up to about 50 mole %, based on the amount in moles of MAHC present. Higher catalysts concentrations may be desirably employed to reduce the reaction time and minimize the size of process equipment.

In a preferred embodiment, the mixture distilled or fractionated in step (a) comprises water, such as the water produced as a co-product of the hydrochlorination reaction, water present in the starting materials for the hydrochlorination reaction, and/or water introduced as the stripping agent. The mixture (a) may contain at least about 1, more preferably at least about 5, weight-percent water up to about 80, preferably up to about 50, more preferably up to about 20, and most preferably up to about 10, weight-percent water.

The mixture of step (a) may be a combination of liquid phase and vapor phase. The mixture of step (a) is preferably provided to the separation step as a liquid phase as opposed to a gaseous or vapor phase.

In one embodiment, the mixture of step (a) is provided to step (b) by separating a hydrochlorination reaction effluent stream into a vapor-phase effluent stream and a liquid-phase effluent stream prior to step (b) and introducing the liquid-phase effluent stream or both the vapor-phase effluent stream and the liquid-phase effluent stream, separately or combined, into step (b). The separation of the reaction effluent stream may be carried out in, for example, a flash vessel separate from or integral with step (b).

Recovery of DCH from the Mixture (a):

Recovery of DCH according to the present invention takes place in two steps. First, the mixture (a) is distilled and/or fractionated to separate a lower boiling fraction comprising dichlorohydrin(s) from the mixture of step (a) to form a higher boiling fraction comprising the residue of the distillation or fractionation. DCH(s), and preferably water, may be recovered from the lower boiling fraction of step (b).

Then the residue of the first distillation and/or fractionation is distilled and/or fractionated (c) to separate dichlorohydrin(s) from the mixture of the higher boiling fraction of step (b) to produce a vapor fraction enriched with DCH(s). Distillation and/or fractionation step (c) is preferably carried out on the higher boiling fraction produced in step (b) after removing the higher boiling fraction produced in step (b) from the distillation or fractionation step (b).

Since the first distillation residue is distilled and/or fractionated in distillation or fractionation step (c), step (b) may be conducted under milder separation conditions than those required to optimize DCH recovery. DCH(s), and preferably water, may be recovered from the lower boiling fraction of step (b). The temperature and pressure for step (b) are preferably adjusted to recover at least about 1, more preferably at least about 10, even more preferably at least about 25, and yet more preferably at least about 50, and up to about 99, more preferably up to about 95, yet more preferably up to about 90, yet even more preferably up to about 80, and even more preferably up to about 70, weight-percent of the total amount of DCH in the mixture provided in step (a) via the lower boiling fraction produced in step (b).

Milder separation conditions may include reducing the temperature of the distillation bottoms to reduce energy consumption and reduce the rate of heavy byproduct formation during step (b). Safety and efficiency are improved when the distillation column is operated at lower bottom temperature.

Distillation or fractionation step (b) is preferably carried out at a temperature measured in the distillation bottoms of at least about 25° C., more preferably at least about 50° C., yet more preferably at least about 80° C., even more preferably at least about 100° C., and yet even more preferably at least about 110° C., up to about 200° C., more preferably up to about 160° C., yet more preferably up to about 140° C., even more preferably up to about 139° C., yet even more preferably up to about 135° C., yet even more preferably up to about 132° C., yet even more preferably up to about 125° C., and yet even more preferably up to about 120° C.

Milder separation conditions may also include operation of step (b) under pressure conditions higher than those used in conventional processes for separating DCH(s) from reactor effluents. The higher pressure condition process allows for energy savings and a wider selection of vacuum devices. A more economical steam jet ejector or vacuum pump can be used, which reduces fixed capital and operating costs. Operational reliability is also improved through the use of steam-jet ejectors, because steam-jet ejectors do not have moving parts, while low pressure, high vacuum operation generally requires the use of rotary oil-sealed vacuum pumps or multiple stages of steam-jet ejectors. Also higher distillation column pressure operation reduces column size, thereby reducing the capital investment to be amortized.

The distillation or fractionation step (b) is preferably carried out at a pressure of at least about 0.1 kPa, more preferably at least about 1 kPa, even more preferably at least about 3 kPa, yet more preferably at least about 6 kPa, and even more preferably at least about 10 kPa, up to about 1 MPa, more preferably up to about 0.12 MPa, yet more preferably up to about 0.05 MPa, and even more preferably up to about 0.02 MPa.

The percent DCH(s) recovered from the mixture introduced into step (b) generally depends on the combination of temperature and pressure conditions selected. To obtain a given DCH recovery in step (b), a reduction in temperature generally requires a reduction in operating pressure and an increase in operating pressure, conversely, generally requires an increase in operating temperature. The specific temperature and pressure conditions selected will depend on the extent to which realization of the respective benefits relating to low temperature and higher pressure operation is desired.

Step (b) is preferably carried out under conditions such that the amount of heavy byproducts in the high boiling fraction of step (b) does not exceed about 110 percent, more preferably not more than about 108 percent, even more preferably not more than about 105 percent, and even more preferably not more than about 102 percent, of the amount of heavy byproducts in the mixture provided in step (a).

The conditions during step (b) are preferably adjusted to produce a higher boiling fraction containing less than about 50, more preferably less than about 20, even more preferably less than about 10, and yet even more preferably less than about 5, percent of the chlorinating agent(s) present in the mixture provided in step (a). One or more conditions of step (b), such as the temperature and pressure, may be adjusted to remove chlorinating agent(s) from the mixture (a) provided to step (b).

In one embodiment a portion of hydrogen chloride is removed from the liquid effluent prior to step (b) via a reduction in pressure permitting escape of hydrogen chloride dissolved in the liquid effluent; and preferably at least 50 percent of the hydrogen chloride is removed from the liquid phase effluent prior to step (b).

When the chlorinating agent is hydrogen chloride for example, the hydrogen chloride may be removed from the mixture (a) during step (b) by maintaining a pressure during step (b) that is below the pressure required to maintain dissolution of the hydrogen chloride present in the mixture provided in step (a) and/or maintaining a temperature during step (b) that is greater than the temperature required to maintain dissolution of the hydrogen chloride present in the mixture provided in step (a).

In a preferred embodiment, the mixture provided in step (a) is passed through a pressure letdown step for degassing the mixture prior to distilling and/or fractionating the mixture. When there are flow fluctuations or surges upstream from the distillation and/or fractionation step, the pressure letdown step and/or a surge vessel may also be used to help regulate the flow of the mixture into the distillation and/or fractionation step.

Step (b) is preferably carried out in a distillation column, such as a fractional distillation column. Examples of suitable distillation columns include a plate or tray columns, bubble cap columns and packed columns. Preferably step (b) of the present process is carried out using a packed distillation column.

In one embodiment, additional MAHC(s) and/or ester(s) thereof may be introduced into step (b) for reactive distillation/fractionation. The additional MAHC(s) and/or ester(s) thereof may react with the chlorination agent to produce additional MCH(s) and/or ester(s) thereof. Additional MAHC(s) may also react with ester(s) of DCH(s) and MCH(s) to convert them to non-ester(s) to facilitate recovery of DCH(s). The additional MAHC(s) and/or ester(s) thereof is/are preferably introduced as a liquid phase into a reflux to provide additional liquid phase for reflux.

In a preferred embodiment, step (b) comprises:
(b1) vaporizing an azeotropic mixture comprising DCH(s) and water from the mixture of step (a) to separate a lower boiling fraction comprising at least DCH(s) and water from the mixture of step (a); and
(b2) condensing the low boiling fraction of step (b1) to form a liquid aqueous phase and a liquid organic phase comprising DCH(s).

The condensing step (b2) may comprise refluxing in a distillation column, such as a fractional distillation column and/or a packed distillation column.

In one embodiment, additional MAHC(s) and/or ester(s) thereof may be introduced into condensing step (b2) for reactive distillation/fractionation for the reasons stated above. Such addition also increases the amount of liquid available for reflux during distillation/fractionation, which increases the efficiency with which step (b) separates DCH and water from the other components of the mixture (a) provided to step (b).

Step (b) may further comprise:
(b3) separating the liquid aqueous phase of step (b2) from the liquid organic phase of step (b2); and
(b4) recycling at least some of the liquid aqueous phase of step (b3) to step (b1) and/or step (b2).

Recycling the liquid aqueous phase to step (b1) may be used to facilitate recovery of DCH by azeotroping and/or stripping DCH(s) from the reaction mixture.

Recycling the liquid aqueous phase to step (b2) may be used to provide additional liquid for reflux during step (b). When sufficient liquid aqueous phase is recycled to step (b2), the liquid aqueous phase may flow to the bottom of the distillation/fraction apparatus, so that at least some of the same liquid aqueous phase is also recycled to step (b1) where it may also facilitate recovery of DCH by azeotroping and/or stripping DCH(s) from the reaction mixture.

In step (c), the higher boiling fraction produced by step (b) may be distilled or fractionated at a higher or lower pressure than in step (b). Distillation or fractionation step (c) is preferably carried out at a temperature measured in the distillation bottoms of at least about 25° C., more preferably at least about 50° C., yet more preferably at least about 80° C., even more preferably at least about 100° C., and yet even more preferably at least about 110° C., up to about 200° C., more preferably up to about 170° C., yet more preferably up to about 140° C., even more preferably up to about 139° C., yet even more preferably up to about 135° C., yet even more preferably up to about 132° C., yet even more preferably up to about 125° C., and yet even more preferably up to about 120° C.

The distillation or fractionation step (c) is preferably carried out at a pressure of at least about 0.1 kPa, more preferably at least about 1 kPa, even more preferably at least about 3 kPa, yet more preferably at least about 6 kPa, and even more preferably at least about 10 kPa, up to about 1 MPa, more preferably up to about 0.12 MPa, yet more preferably up to about 0.05 MPa, and even more preferably up to about 0.02 MPa. For economic reasons, step (c) may be carried out at atmospheric pressure.

In one embodiment, the process of the present invention steps (b) or (c) are carried out at a pressure in the range from about 0.1 kPa to about 0.2 Mpa; and preferably in the range from about 1 kPa to about 0.05 Mpa; and the temperature of the higher boiling fraction during steps (b) or (c) is in the range from about 50° C. to about 169° C.; and preferably in the range from about 90° C. to about 139° C.

Step (c) may further comprise distilling or fractionating the vapor fraction of step (c) for isolating dichlorohydrin(s), and/or stripping agent.

The lower boiling fraction produced by step (b) and the vapor fraction produced in step (c) recovered in step (d) may be recovered separately and subjected to further processing steps or they may be combined. Depending on the further processing steps, the lower boiling fraction and/or the vapor fraction may be used separately or combined to supply DCHs for chemical conversion into other compounds without further processing. The lower boiling fraction/vapor fraction mixture may be used in processes for conversion of DCH(s) into other industrially useful chemical products.

The lower boiling fraction and/or the vapor fraction recovered in step (d) may, for example, be subjected to epoxidation to form epichlorohydrin without additional purification of the dichlorohydrin(s) other than via the above-described optional liquid-liquid phase separation for recycling an aqueous phase in step (b3) or via the above-described optional distillation or fractionation of the vapor fraction produced during step (c).

Any combination of the above process steps may be carried out independently or simultaneously with one another. In a preferred embodiment, one or more of the above process steps is carried out simultaneously with one another.

One or more of the above process steps may be carried out continuously or discontinuously. One or more of the above process steps are preferably carried out continuously (i.e., without interruption) for a predetermined period of time, for example, for a time period of at least one hour. Preferably, all the above process steps are carried out continuously for a time period of, for example, at least one hour.

At least some of the higher boiling fraction treated in step (c) is preferably recycled to a hydrochlorination step. In a more preferred embodiment, substantially all the higher boiling fraction treated in step (c) is recycled to a hydrochlorination step. The hydrochlorination step is preferably the first step in the hydrochlorination process used to produce a hydrochlorination effluent containing components of the mixture (a).

Recycling the treated higher boiling fraction permits further reaction of MAHC(s) and/or ester(s) thereof and/or MCH(s) and/or ester(s) thereof to form additional DCH, which generally increases the overall hydrochlorination conversion and recovery rates. In that case, the process according to the present invention may recover at least 80 percent, more preferably at least about 90 percent, even more preferably at least about 95 percent, yet more preferably at least about 99 percent, and yet even more preferably at least about 99.9 percent of the DCH(s) produced during hydrochlorination.

The above process may be conducted using an apparatus according to the present invention. The apparatus is now described in more detail in reference to FIG. 1.

FIG. 1 is a block flow diagram showing the main features of an illustrative apparatus that may be used and their respective feed streams. The apparatus, generally indicated by numeral 100 in FIG. 1 comprises at least one reactor (10); at least one first separation device (20) comprising at least one first liquid-vapor contacting device having a bottom end and a top end for applying a gradually decreasing temperature gradient from the bottom end to the top end to substances within the separation device (20); and at least one second separation device (30) comprising at least one second liquid-vapor contacting device (30) for further separating the higher boiling fraction that is produced in separation device (20).

The at least one reactor (10) may be selected from various known reactors, such as CSTRs, tubular reactors, column reactors, and PFRs, and combinations thereof. When multiple reactors are present, the reactors may be connected to each other in series or parallel. The at least one reactor (10) is connected directly or indirectly to a first feed stream (11) comprising MAHC(s) and, optionally, a catalyst feed; and a second feed stream (12) comprising chlorinating agent.

The at least one reactor (10) is connected directly or indirectly to the at least one first separation device (20) for conducting at least part of a reactor effluent feed stream (13) from the at least one reactor (10) to the at least one first liquid-vapor contacting device of the separation device (20) for distillation and/or fractionation. The connection for conducting a reactor effluent feed stream (13) from the at least one reactor (10) is preferably adapted to conduct a liquid-phase feed stream from the at least one reactor (10). Any inert gas accumulation in the at least one reactor (10) is purged via reactor vent gas stream (14).

The at least one first separation device (20) comprises a first port (21) for recovering an effluent stream comprising DCH(s) separated from the reactor effluent feed stream (13) via the at least one first liquid-vapor contacting device of the separation device (20) and preferably comprises a first vent (22) for removing gases at the top of the at least one first liquid-vapor contacting device of the separation device (20).

In one embodiment the at least one first separation device (20) preferably comprises a means for applying a vacuum to the at least one first liquid-vapor contacting device of the at least one separation device (20) for reducing the pressure in the at least one first separation device (20) below ambient atmospheric pressure. The means is preferably a steam-jet ejector.

In another embodiment the at least one separation device (20) operates near or above atmospheric pressure.

In one embodiment of the present invention, the at least one first liquid-vapor contacting device of the at least one first separation device (20) is preferably a distillation or fractionation column, such as a packed distillation column and/or a distillation column adapted for carrying out fractional distillation under reflux conditions having a reflux zone for carrying out rectification.

In another illustrative embodiment of the present invention, the at least one first separation device (20) preferably comprises at least one flash vessel and the at least one reactor (10) is connected to at least one first liquid-vapor contacting device of the at least one separation device (20) via the at least one flash vessel, whereby the feed stream conducted from the at least one reactor (10) is separated into a vapor phase and a liquid phase in the flash vessel by reducing the pressure on the liquid phase and the separated liquid phase is introduced into the first liquid-vapor contacting device of separation device (20) for distillation or fractionation.

The at least one first separation device (20) also preferably comprises a reboiler connected to the at least one first liquid-vapor contacting device of the at least one separation device (20) for heating the feed stream(s) conducted to the at least one first liquid-vapor contacting device of the at least one separation device (20).

The at least one first separation device (20) is connected directly or indirectly to the at least one second separation device (30) for conducting a distilled or fractionated liquid bottoms feed stream (23) from the at least one first liquid-vapor contacting device of the separation device (20) to the at least one second liquid-vapor contacting device (30) for further distillation and/or fractionation. The at least one first separation device (20) has a first port (21) for recovering a dichlorohydrin(s)-containing distillate.

The at least one second separation device (30) comprising the at least one second liquid-vapor contacting device (30) is connected directly to liquid residue feed stream (23), the at least one second liquid-vapor contacting device (30) having at least one second port (31) for recovering a dichlorohydrin(s)-containing product stripped from a distilled or fractionated liquid residue delivered to the second liquid-vapor contacting device (30) via liquid residue feed stream (23). The second liquid-vapor contacting device (30) preferably has a third port (32) for withdrawing liquid residue feed stream from the second liquid-vapor contacting device (30).

The third port (32) is preferably connected to the at least one reactor (10) via recycle conduit (33) for conducting a recycle feed stream comprising a distillation fraction from the at least one second liquid-vapor contacting device (30) to the at least one reactor (10). The recycle conduit (33) preferably has a purge (34) for removal of heavy byproducts from the recycle feed stream.

The second liquid-vapor contacting device (30) is preferably at least one column and is more preferably a distillation column. The distillation column is preferably adapted for carrying out fractional distillation under reflux conditions having a reflux zone for carrying out rectification. The effluent stream (31) is preferably a distillate obtainable with such a distillation column.

In one embodiment, the apparatus of the present invention includes a liquid-liquid phase separator connected, directly or via a cooling device, to the reflux zone of the distillation column(s) for separating a condensed liquid aqueous phase from a condensed liquid organic phase and for conducting the liquid aqueous phase from the liquid-liquid phase separator to the reflux zone of the distillation column(s).

The apparatus may further comprise one or more distillation columns, extraction columns, absorption columns, reboilers, and condensers, and combinations thereof, connected with the at least one reactor (10) and/or the at least one first column (20). The second vapor-liquid contacting device (30) may comprise a steam stripper.

The at least one first separation device (20) of the present invention may comprises a reboiler connected to the at least one first liquid-vapor contacting device of the at least one separation device (20) for heating the feed stream(s) conducted to the at least one first liquid-vapor contacting device of the at least one separation device (20).

The second liquid-vapor contacting device (30) preferably has a second vent (35) for conducting a vapor phase effluent from the top of the second liquid-vapor contacting device (30).

Figure 2:
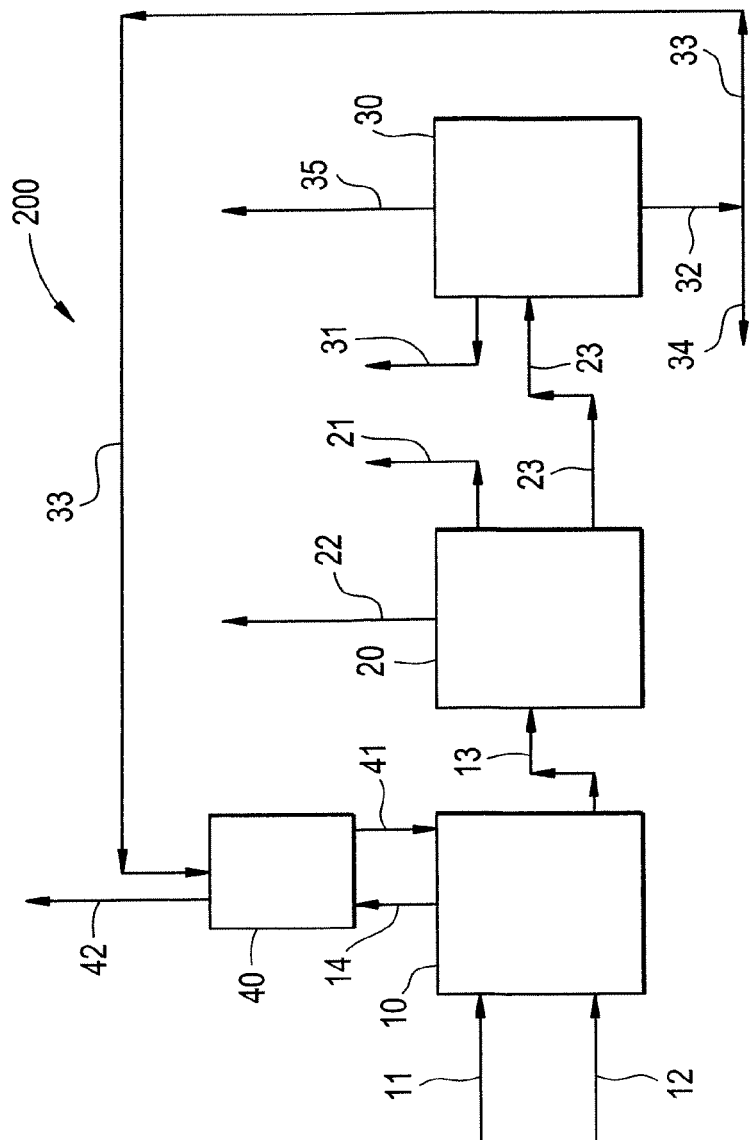
FIG. 2 is a process diagram illustrating another embodiment of the process of the present invention.

Another embodiment of the present invention is shown in FIG. 2 wherein the apparatus generally indicated by numeral 200, is essentially the same as in FIG. 1 except that the block (10) indicating the at least one reactor (10) may also comprise an absorption system (40) for a vent gas (14) leaving the reactor (10). The process embodiment shown in FIG. 2 is similar to the system described in U.S. Provisional Patent Application Ser. No. 60/923,019, entitled "PROCESS AND APPARATUS FOR VAPOR PHASE PURIFICATION DURING HYDROCHLORINATION OF MULTI-HYDROXYLATED ALIPHATIC HYDROCARBON COMPOUNDS" filed Apr. 12, 2007 by Hook et al., (Attorney Docket No. 65647), incorporated herein by reference.

FIG. 2 illustrates an extension of FIG. 1 wherein an absorption system (40), an absorption system liquid effluent stream (41), and an absorption system vent stream (42) are preferably added to the system. The embodiment specifically shown in FIG. 2 includes a recycle conduit (33) which may also connect to the at least one reactor (10) via the absorption system (40) for absorbing chlorinating agent in the reactor vent gas (14) leaving from the at least one reactor (10) as described in the U.S. Provisional Patent Application Ser. No. 60/923,019 above. The absorption system liquid effluent (41) from the absorption system (40) is fed to the at least one reactor (10) as the part of the feed for the at least one reactor (10). Any non-absorbable and inert gases in the absorption system (40) may be purged via the absorption system vent gas stream (42). The rest of the process equipment and streams shown in FIG. 2 may be the same as described in FIG. 1.

Figure 3:
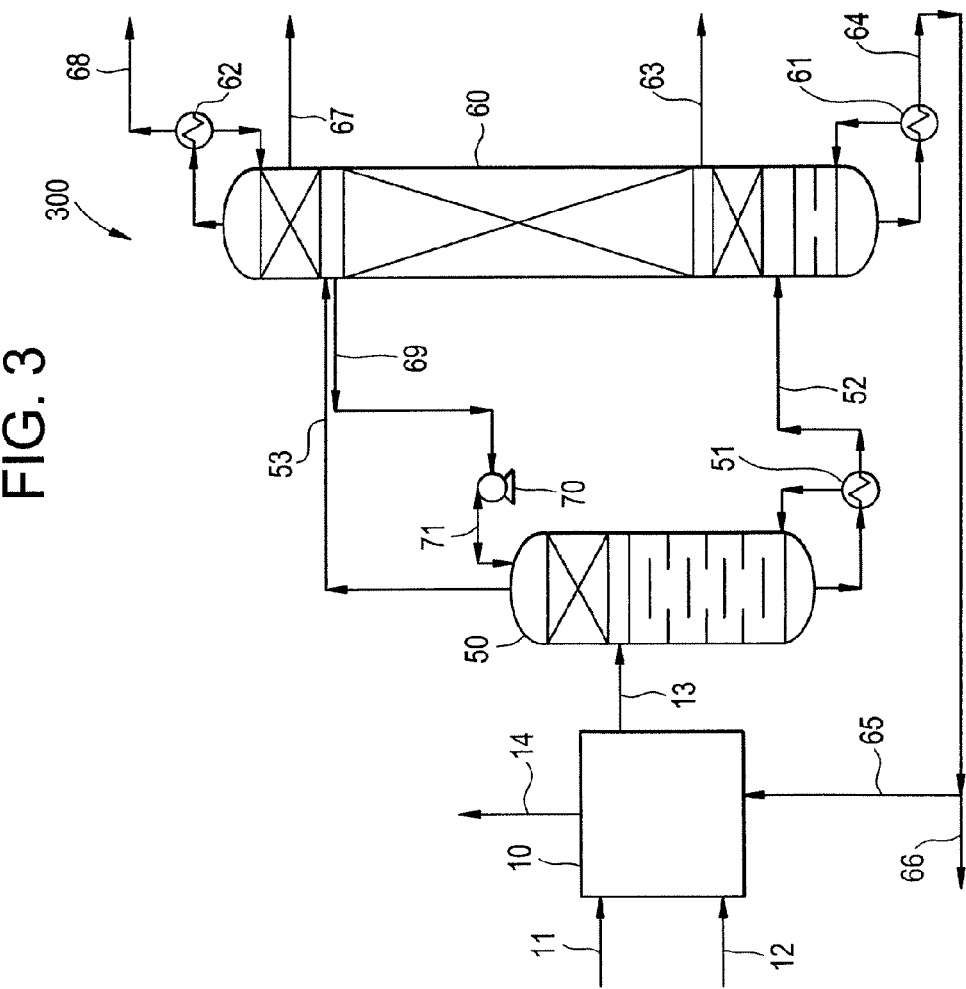
FIG. 3 is a process diagram illustrating another embodiment of the process of the present invention.

FIG. 3 is a process flow diagram showing the main features of an illustrative apparatus and their respective feed streams that may be used for separating dichlorohydrin(s) from a mixture comprising dichlorohydrin(s), one or more compounds selected from ester(s) of chlorohydrin(s), monochlorohydrin(s), and/or multihydroxylated-aliphatic hydrocarbon compound(s) and/or ester(s) thereof, and optionally one or more substances comprising water, chlorinating agent(s), catalyst(s), ester(s) of catalyst(s), and/or heavy byproduct(s); or similar mixtures comprising light boiling components, middle distillate components, and heavy boiling components. The dichlorohydrins may comprise part of any of these three streams. The advantage of the configuration shown in FIG. 3 is reduced energy consumption for equivalent separation of the feed.

With reference to FIG. 3 again, the apparatus, generally indicated by numeral 300, comprises at least one reactor (10); at least one first separation device (50) comprising at least one first liquid-vapor contacting device having a bottom end and a top end for applying a gradually decreasing temperature gradient from the bottom end to the top end to substances within the column; and at least one second separation device (60) comprising at least one second liquid-vapor contacting device (60) for contacting a liquid phase material with vapor phase of liquid bottoms feed stream (52) from the at least one first liquid-vapor contacting device of the separation device (50) to the at least one second liquid-vapor contacting device of the separation device (60) or a stripping agent for further distillation and/or fractionation. The particular implementation of the present invention shown in the FIG. 3 also includes at least one internal or external reboiler (51) in the separation device (50). The second separation device (60) shown in FIG. 3 may have also at least one external or internal reboiler (61). At least one internal or external condenser (62) can be also used in the separation device (60). A pressure changer device (70), for example a pump (70), can be used to direct liquid stream (69) from the second separation device (60) to the first separation device (50) via stream (71).

The at least one reactor (10) may be selected from various known reactors, such as CSTRs, tubular reactors, column reactors and PFRs, and combinations thereof. When multiple reactors are present, the reactors may be connected to each other in series or parallel. At least one reactor (10) is connected directly or indirectly to a first feed stream (11) comprising MAHC(s) and a second feed stream (12) comprising chlorinating agent. Any inert gas accumulation in the at least one reactor (10) may be purged via reactor vent gas stream (14).

The at least one reactor (10) is connected directly or indirectly to the at least one first separation device (50) for conducting at least part of a reactor effluent feed stream (13) from the at least one reactor (10) to the at least one first liquid-vapor contacting device of separation device (50) for distillation and/or fractionation. The connection for conducting a reactor effluent feed stream (13) from the at least one reactor (10) is preferably adapted to conduct a liquid-phase feed stream from the at least one reactor (10).

The at least one first separation device (50) comprises a first port for recovering an effluent stream (53) comprising low boiling vapor(s) separated from the reactor effluent feed stream (13) via the at least one first liquid-vapor contacting device of separation device (50) and preferably comprises a second port for taking liquid stream (69,71) from an upper stage of an at least one additional separation device, such as the at least one second separation device (60), and pumping that liquid back to the top of the at least one first liquid-vapor contacting device of the separation device (50).

The at least one separation device (50) preferably comprises a means for applying a vacuum to the at least one first liquid-vapor contacting device of the at least one first separation device (50) for reducing the pressure in the at least one first liquid-vapor contracting device of the at least one first separation device (50) below ambient atmospheric pressure. The means for applying the vacuum is preferably a steam-jet ejector.

In one embodiment, the at least one first liquid-vapor contacting device of the at least one separation device (50) is preferably a distillation or fractionation column, such as a packed distillation column and/or a distillation column adapted for carrying out fractional distillation under reflux conditions having a reflux zone for carrying out reflux. In this embodiment, the reflux is the liquid stream (69,71) coming back to the top of the column (50).

In another illustrative embodiment of the present invention, the at least one first separation device (50) preferably comprises at least one flash vessel and the at least one reactor (10) is connected to at least one first liquid-vapor contacting device of the at least one separation device (50) via the at least one flash vessel, whereby the feed stream conducted from the reactor (10) is separated into a vapor phase and a liquid phase in the flash vessel by reducing the pressure on the liquid phase and the separated liquid phase is introduced into the first liquid-vapor contacting device of separation device (50) for distillation or fractionation.

The at least one first separation device (50) also preferably comprises a reboiler connected to the at least one first liquid-vapor contacting device of the at least one separation device (50) for heating the feed stream(s) conducted to the at least one first liquid-vapor contacting device of the at least one separation device (50).

The at least one first separation device (50) is connected directly or indirectly to the at least one second separation device (60) for conducting a distilled or fractionated liquid bottoms feed stream (52) from the at least one first liquid-vapor contacting device of the separation device (50) to the at least one second liquid-vapor contacting device of the separation device (60) for further distillation and/or fractionation. The at least one second separation device (60) has a port for recovering a medium boiling distillate (63) which may comprise a dichlorohydrin(s)-containing distillate.

The at least one second liquid-vapor contacting device (60) is connected directly to liquid residue feed stream (52), the at least one second liquid-vapor contacting device (60) having at least one second port for recovering a dichlorohydrin(s)-containing product in stream (63) stripped from a distilled or fractionated liquid residue delivered to the second liquid-vapor contacting device (60) via liquid residue feed stream (52). The second liquid-vapor contacting device (60) preferably has a third port for withdrawing liquid residue feed stream (64) from the second liquid-vapor contacting device (60).

The liquid stream from the third port (64) is preferably connected to the at least one reactor (10) via recycle conduit (65) for conducting a recycle feed stream comprising a distillation fraction from the at least one second liquid-vapor contacting device (60) to the at least one reactor (10). The recycle conduit (65) preferably has a purge (66) for removal of heavy byproducts from the recycle feed stream.

The recycle conduit (65) may also connect to the at least one reactor (10) via an absorption system for vent gas leaving the reactor as described in the U.S. Provisional Patent Application Ser. No. 60/923,019 above.

In one embodiment, the second liquid-vapor contacting device (60) is preferably a column and is more preferably a distillation column. The distillation column is preferably adapted for carrying out fractional distillation under reflux conditions having a reflux zone for carrying out reflux. The effluent streams (67) and (68) are preferably distillates obtainable with such a distillation column.

The second liquid-vapor contacting device (60) preferably has a second vent (68) for conducting a vapor phase effluent from the top of the second liquid-vapor contacting device (60).

To the extent that components of the above apparatus are exposed to corrosive materials, such components are preferably fabricated of materials which are resistant to corrosion by the process components. *Kirk-Othmer Encyclopedia of Chemical Technology*, $2^{nd}$ Edition (John Wiley and Sons, 1966), volume 11, pages 323-327, presents an extensive discussion of the corrosion resistance of metals and non-metals that can be used in hydrochloric acid and hydrogen chloride service. Specific examples of suitable materials are disclosed in WO 2006/020234 and U.S. Provisional Patent Application Ser. No. 60/923,055, entitled "CONVERSION OF A MULTIHYDROXYLATED-ALIPHATIC HYDROCARBON OR ESTER THEREOF TO A CHLOROHYDRIN" filed Apr. 12, 2007, by Briggs et al., incorporated herein by reference. Specific examples include metals such as tantalum, or suitable metallic alloys (particularly nickel-molybdenum alloys such as Hastelloy C™); fluoroelastomer-lined equipment; or glass-lined equipment.

When milder temperature conditions are used to recover DCH according to the present invention, less expensive corrosion-resistant materials may be used in one or more components of the apparatus downstream from the reactor(s), such as distillation or fractionation column(s) (50), the second liquid-vapor contacting device (60) and/or components and conduits linking those components to each other or to other downstream components. This reduces the capital investment cost for building a production facility to be amortized, which reduces the overall cost of the process according to the present invention.

The following examples are for illustrative purposes only and are not intended to limit the scope of the present invention.

Equipment Used in the Examples

Distillation is carried out using a glass distillation column packed with 6 mm ceramic Intalox saddles, containing two packed bed sections. Feed to the column is located between the two packed bed sections. The column is provided with a glass reboiler and two partial condensers in series, also made of glass, for cooling the vapor stream exiting the column. The first condenser is cooled with chilled glycol. A portion of the condensate from the first condenser is returned to the column as reflux and the rest of the condensate is collected as product.

Uncondensed vapors from the first condenser are condensed in the second condenser operating at a lower temperature and cooled with chilled glycol. The uncondensed vapors exiting the second condenser are passed through a set of cold traps before entering a vacuum pump which provides vacuum to the whole system. The second condensed liquid-phase effluent from the second condenser is collected as product.

In Example 1, two columns are connected in series, meaning, the first distillation residue is fed to a second distillation column. The second distillation column has the same dimensions to those of the above-described distillation column. The data for this Example 1 are generated from a computer simulation based on actual data obtained from the glass distillation column.

In Example 2, two columns are connected in a heat integrated configuration. The suggested configuration can be considered a non-adiabatic modification of so-called Petlyuk distillation scheme without vapor split. The suggested configuration is different from the Petlyuk distillation schemes or dividing wall distillation schemes due to inclusion of additional reboiler at the first distillation column so-called prefractionator column. This difference eliminates the vapor flow from main column to prefractionator column required in the known Petlyuk type distillation schemes. This in turns performs the process at different pressures in the prefractionator column and main column. This is one of the major advantages of the separation scheme described in the example. A compressor or blower will be required to operate classical Petlyuk separation scheme at the conditions when the pressures are different in prefractionator and main column. The data for this Example 2 are generated from a computer simulation based on actual data obtained from the glass distillation column.

In Example 3, actual data are obtained from the glass distillation column at two different operation conditions to verify the computer simulation data obtained in Example 1.

Composition and Conditions of Feed Stream Mixture (A)

The feed stream composition and conditions shown in Table 1 below are used to provide the mixture (a) for each example:

TABLE 1

| Conditions and Composition | | Units |
|---|---|---|
| Feed Rate | 5.15 | kg/hr |
| Feed Temperature | 100 | ° C. |
| Feed Pressure | 105.1 | kPa |
| Feed Composition: | | |
| Hydrogen chloride | 3.3 | Weight-percent |
| Water | 10.2 | Weight-percent |
| 1,3-dichloro-2-propanol | 32.6 | Weight-percent |
| 2,3-dichloro-1-propanol | 7.0 | Weight-percent |
| 3-chloro-1,2-propanediol | 8.0 | Weight-percent |
| 2-chloro-1,3-propanediol | 12.1 | Weight-percent |
| Esters | 11.5 | Weight-percent |
| Glycerol | 15.3 | Weight-percent |

As shown in Table 1 above, the 1,3-dichloro-2-propanol rate is 32.6 weight-percent of the 5.15 kg/hr feed rate or 1.67 kg/hr and the 2,3-dichloro-1-propanol rate is 7.0 weight-percent of the 5.15 kg/hr feed rate or 0.36 kg/hr. The sum of the 1,3-dichloro-2-propanol feed rate (1.67 kg/hr) and 2,3-dichloro-1-propanol feed rate (0.36 kg/hr), is 2.03 kg/hr.

Example 1

In this Example 1, a DCH recovery process is carried out according to the present invention using the feed composition and conditions shown in Table 1 above. The first distillation is carried out under moderate vacuum conditions followed by the second distillation column, which is carried out under low vacuum conditions.

The distillation column process conditions used in Example 1 are shown in Table 2 below:

TABLE 2

| Distillation Column Process Conditions | | | |
|---|---|---|---|
| Distillation column | First | Second | Units |
| Condenser temperature | 42.0 | 25.5 | ° C. |
| Condenser pressure | 5.3 | 1.3 | kPa |
| Bottom temperature | 114.0 | 114.0 | ° C. |
| Reflux ratio (reflux rate/distillate rate) | 0.28 | 0.33 | |
| Distillate to feed ratio | 0.18 | 0.35 | |
| Pressure drop across the column | 1.3 | 1.3 | kPa |

Using a computer simulation based on actual data obtained in Comparative Example A, the first distillation data shown in Table 3 are obtained.

TABLE 3

| Subject | Vent | Overheads | Bottoms | Units |
|---|---|---|---|---|
| Rate | * | 0.93 | 4.2 | kg/hr |
| Heat Duty | | −0.049 | 0.438 | kW |
| HCl | 68.19 | 18.23 | * | wt. % |
| H$_2$O | 20.56 | 56.89 | * | wt. % |
| 1,3-dichloro-2-propanol | 10.85 | 23.84 | 34.54 | wt. % |
| 2,3-dichloro-1-propanol | 0.41 | 1.05 | 8.30 | wt. % |
| 3-chloro-1,2-propanediol | * | 0.01 | 42.84 | wt. % |
| 2-chloro-1,3-propanediol | * | 0.01 | 9.80 | wt. % |
| glycerin | * | * | 18.68 | wt. % |

In Table 3 above, "Vent" refers to stream 22 in FIG. 1. "Overheads" refers to the stream 21 of FIG. 1. "Bottoms" refers to the distillation residue stream 23 of FIG. 1. Asterisk ("*") indicates that the weight-percent value was below 0.01. "Heat Duty" refers to the energy added to or removed from the corresponding stream. Negative sign ("−") in front of the numbers refers to the removal of energy from the corresponding stream.

As shown in Table 3 above, the 1,3-dichloro-2-propanol rate is 34.54 weight-percent of the 4.20 kg/hr feed rate or 1.45 kg/hr and the 2,3-dichloro-1-propanol rate is 8.30 weight-percent of the 4.20 kg/hr feed rate or 0.35 kg/hr. The sum of the 1,3-dichloro-2-propanol feed rate (1.45 kg/hr) and 2,3-dichloro-1-propanol feed rate (0.35 kg/hr), is 1.80 kg/hr.

The rate at which DCH is recovered in the overheads via the first distillation step (b) may be calculated as the difference between the DCH feed rate (2.03 kg/hr as shown in the explanation for Table 1) and the DCH bottoms rate (1.80 kg/hr) or 0.23 kg/hr.

DCH recovery in the first distillation is therefore 11.3 percent (0.23÷2.03×100).

The distillation residue, referred to as the "bottoms" in Table 3, is used as the feed stream for computer simulated second distillation column. The simulated second distillation column pressure is kept at 1.3 kPa. The results obtained are shown below in Table 4.

TABLE 4

| Subject | Overheads | Bottoms | Units |
|---|---|---|---|
| Rate | 1.46 | 2.76 | kg/hr |
| Heat Duty | −0.249 | 0.194 | kW |
| 1,3-dichloro-2-propanol | 85.96 | 7.35 | wt. % |
| 2,3-dichloro-1-propanol | 14.04 | 5.32 | wt. % |
| 3-chloro-1,2-propanediol | * | 12.67 | wt. % |
| 2-chloro-1,3-propanediol | * | 14.97 | wt. % |
| glycerin | * | 28.57 | wt. % |

From the above data in Table 4, the DCH overheads rate may be calculated by adding the weight-percent values for 1,3-dichloro-2-propanol and 2,3-dichloro-1-propanol, dividing the sum by 100, and multiplying the resulting value with the 1.46 kg/hr overheads rate to obtain 1.46 kg/hr.

The DCH feed rate to the second distillation column equals to the DCH bottoms rate of the first distillation (1.80 kg/hr as shown in the explanation for Table 3).

DCH recovery from the second column is therefore 81.1 percent (1.46÷1.80×100).

The total DCH rate at which DCH is recovered in the overheads via the first distillation step (b) and second distillation step (c) is 1.69 kg/hr (0.23+1.46).

DCH recovery obtained with the first distillation combined with the second distillation column is therefore 83.3 percent (1.69÷2.03×100).

From Table 3 and 4, the total heat duties of the first distillation column bottoms combined with the second distillation column bottoms are 0.632 kW (0.438+0.194). The total heat duties of the combined distillation column bottoms per kg of total DCH recovered is 0.374 kWh/kg of DCH (0.632/1.69). Similarly, the total heat duties of the first distillation column overheads combined with the second distillation column overheads are −0.298 kW (−0.049-0.249). The total heat duties of the combined distillation column overheads per kg of total DCH recovered is −0.176 kWh/kg of DCH (−0.298/1.69).

Comparative Example A

In this Comparative Example A, DCH recovery and heat duties are determined based on the conventional high vacuum distillation process using the Example 1 distillation equipment and distillation feed stream where two of identical distillation columns are connected in parallel manner, each distillation column receives half of the feed provided in Example 1. The distillation conditions are modified to maximize DCH recovery during distillation by reducing the condenser pressure and adjusting the condenser temperature to take the lower condenser pressure into account while maintaining the same bottom temperature as shown below in Table 5.

TABLE 5

| Distillation Column Process Conditions | | Units |
|---|---|---|
| Condenser temperature | 12.5 | ° C. |
| Condenser pressure | 1.5 | kPa |
| Bottom temperature | 114.0 | ° C. |
| Reflux ratio (reflux rate/distillate rate) | 0.33 | |
| Distillate to feed ratio | 0.45 | |
| Pressure drop across the column | 1.3 | kPa |

The data obtained with half of the feed of Table 2 fed to the glass distillation column under the above distillation conditions is shown below in Table 6.

TABLE 6

| Subject | Vent | Overheads | Bottoms | Units |
|---|---|---|---|---|
| Rate | 0.07 | 1.09 | 1.42 | kg/hr |
| Heat Duty | | −0.386 | 0.359 | kW |
| HCl | 55.66 | 4.32 | * | wt. % |
| H₂O | 32.74 | 22.13 | * | wt. % |
| 1,3-dichloro-2-propanol | 12.05 | 67.62 | 6.72 | wt. % |
| 2,3-dichloro-1-propanol | 0.55 | 5.93 | 8.08 | wt. % |
| 3-chloro-1,2-propanediol | * | 0.01 | 14.62 | wt. % |
| 2-chloro-1,3-propanediol | * | 0.01 | 22.02 | wt. % |
| glycerin | * | * | 27.85 | wt. % |

The DCH overhead rate may be calculated as 0.80 kg/hr (1.02 kg/hr DCH feed rate minus 0.21 kg/hr DCH bottom rate). DCH recovery is calculated to be 78.4 percent (0.80 kg/hr÷1.02 kg/hr×100), or 4.8% less than in Example 1.

From Table 6, the heat duty of the distillation column bottoms per kg of total DCH recovered is 0.448 kWh/kg of DCH (0.359/0.80) or 1.20 times (0.448/0.374) of similar heat duty of Example 1. Likewise, the heat duty of the distillation column overheads per kg of total DCH recovered is −0.482 kWh/kg of DCH (−0.386/0.80) or 2.74 times (−0.482/−0.176) of similar heat duty of Example 1.

As can be seen from the foregoing, Example 1 according to the present invention is capable of obtaining a recovery of DCH greater than that obtained according to Comparative Example A without imposing a high vacuum condition on the first distillation column. Example 1 is also significantly more energy efficient by operating the first column at moderate vacuum condition, which allows the low boiling component to be removed in the overheads with addition of relatively low heat duty.

Example 2

In this Example 2, a DCH recovery process is carried out according to the present invention using the feed composition and conditions shown in Table 1. The first distillation is carried in the prefractionator under moderate vacuum conditions followed by the main distillation column, which is carried out under low vacuum. The configuration described in this Example 2 is presented in FIG. 3.

The examples modeled using a computer simulation based on actual data. The stream results of the simulation are presented in Table 7 below.

TABLE 7

| | STREAM | | | | | | | | |
|---|---|---|---|---|---|---|---|---|---|
| | 13 | 53 | 52 | 64 | 69 | 63 | 67 | 68 | Units |
| Temperature | 101.4 | 53.0 | 113.5 | 113.4 | 48.9 | 71.8 | 25.5 | 25.5 | ° C. |
| Pressure | 104.8 | 5.3 | 6.7 | 2.7 | 15.9 | 1.8 | 1.3 | 1.3 | kPa |
| Rate | 5.1 | 1.2 | 4.0 | 2.8 | 0.1 | 0.5 | 0.9 | 1.0 | kg/hr |
| HCL | 3.3 | 14 | * | * | * | * | * | 17.5 | wt. % |
| H2O | 10.2 | 43.8 | 0.1 | * | 0.5 | 0 | 2.5 | 51.9 | wt. % |
| 1,3-dichloro-2-propanol | 32.6 | 37.7 | 32.2 | 8.5 | 82.1 | 74.1 | 86.5 | 28.7 | wt. % |
| 2,3-dichloro-1-propanol | 7 | 4.5 | 7.9 | 4.1 | 17.4 | 25.7 | 11.1 | 1.9 | wt. % |
| 3-chloro-1,2-propanediol | 8 | * | 10.3 | 15 | * | 0.1 | * | * | wt. % |
| 2-chloro-1,3-propanediol | 12.1 | * | 15.5 | 22.6 | * | 0.1 | * | * | wt. % |
| glycerin | 15.3 | * | 19.6 | 28.6 | * | * | * | * | wt. % |

Streams 53, 69, 52, 13, 68, 67, 63, and 64 refer to the streams as shown in FIG. 3.

The rate at which DCH is recovered in the overheads via the Petlyuk main distillation step (c) may be calculated as the difference between the DCH feed rate (2.03 kg/hr as shown in the explanation for Table 1) and the DCH bottom rate of the main distillation column stream 64 (0.35 kg/hr) or 1.68 kg/hr.

DCH recovery from the Petlyuk distillation process is therefore 82.7 percent (1.68÷2.03×100) or 4.4 percent better than in the Comparative Example A.

Table 8 shows the combined overhead recovery rate of 68, 67 and 63, heat duty and composition for the Petlyuk distillation process based on the data in Table 7 and results of the computer simulation.

TABLE 8

| Subject | Overheads | Bottoms | Units |
| --- | --- | --- | --- |
| Rate | 2.39 | 2.76 | kg/hr |
| Heat Duty | −0.281 | 0.617 | kW |
| HCL | 7.1 | * | wt. % |
| H2O | 22.1 | * | wt. % |
| 1,3-dichloro-2-propanol | 60.5 | 8.5 | wt. % |
| 2,3-dichloro-1-propanol | 10.2 | 4.1 | wt. % |
| 3-chloro-1,2-propanediol | * | 15 | wt. % |
| 2-chloro-1,3-propanediol | * | 22.6 | wt. % |
| glycerin | * | 28.6 | wt. % |

From Table 8 above, the heat duty of the Petlyuk distillation column bottoms per kg of total DCH recovered is 0.367 kWh/kg of DCH (0.617/1.68). The Comparative Example A would require 1.22 times (0.448/0.367) of similar heat duty. Likewise, the heat duty of the Petlyuk distillation column overheads per kg of total DCH recovered is −0.167 kWh/kg of DCH (−0.281/1.68). The Comparative Example A would require 2.88 times (−0.482/−0.177) of similar heat duty.

The energy consumption of Petlyuk column is significantly lower compare to the energy consumption in the conventional distillation scheme. Among the other advantages in this example is the use of only one condenser for the two columns which decreases the capital cost of the unit. Surprisingly these results were achieved at the increased pressure in the first column without increase of the temperature. The conditions in the first column are same as the previous example. The ability to operate the prefractionator at increased pressure decreases the size of the equipment and leads to capital savings.

Example 3

In this Example 3, a DCH recovery process is carried out on the same glass column described in the Comparative Example A, above, according to the present invention using the feed composition and conditions shown in Table 9 below. The first distillation is carried out under moderate vacuum conditions. To generate the second distillation data under low vacuum conditions similar to the computer simulation described in Example 1, the first distillation column bottoms are collected and used as feed to the same glass distillation column.

TABLE 9

| Conditions and Composition | | Units |
| --- | --- | --- |
| Feed Rate | 2.66 | kg/hr |
| Feed Temperature | 64 | ° C. |
| Feed Pressure | 100.9 | kPa |
| Feed Composition: | | |
| Hydrogen chloride | 2.6 | Weight-percent |
| Water | 8.7 | Weight-percent |
| 1,3-dichloro-2-propanol | 34.7 | Weight-percent |
| 2,3-dichloro-1-propanol | 5.0 | Weight-percent |
| 3-chloro-1,2-propanediol | 14.5 | Weight-percent |
| 2-chloro-1,3-propanediol | 9.1 | Weight-percent |
| Esters | 9.9 | Weight-percent |
| Glycerol | 15.5 | Weight-percent |

As shown in Table 9 above, the 1,3-dichloro-2-propanol rate is 34.7 weight-percent of the 2.66 kg/hr feed rate or 0.92 kg/hr and the 2,3-dichloro-1-propanol rate is 5.0 weight-percent of the 2.66 kg/hr feed rate or 0.13 kg/hr. The sum of the 1,3-dichloro-2-propanol feed rate (0.92 kg/hr) and 2,3-dichloro-1-propanol feed rate (0.13 kg/hr), is 1.05 kg/hr.

The distillation column process conditions used in Example 3 are shown in Table 10 below:

TABLE 10

| Distillation Column Process Conditions | | | |
| --- | --- | --- | --- |
| Distillation column | First | Second | Units |
| Condenser temperature | 23.0 | 17.0 | ° C. |
| Condenser pressure | 33.4 | 1.2 | kPa |
| Bottom temperature | 126.0 | 130.0 | ° C. |
| Reflux ratio (reflux rate/distillate rate) | 0.25 | 0.25 | |
| Distillate to feed ratio | 0.12 | 0.43 | |
| Pressure drop across the column | 0.2 | 0.8 | kPa |

Based on the above operating condition, the first distillation data are obtained as shown in fable 11, below.

TABLE 11

| Subject | Overheads | Bottoms | Units |
| --- | --- | --- | --- |
| Rate | 0.33 | 2.27 | kg/hr |
| HCl | 7.06 | * | wt. % |
| H$_2$O | 61.17 | 2.50 | wt. % |
| 1,3-dichloro-2-propanol | 30.01 | 35.30 | wt. % |
| 2,3-dichloro-1-propanol | 1.42 | 5.60 | wt. % |
| 3-chloro-1,2-propanediol | * | 24.20 | wt. % |
| 2-chloro-1,3-propanediol | * | 10.40 | wt. % |
| glycerin | * | 11.30 | wt. % |

In Table 11 above, "Overheads" refers to the stream 21 of FIG. 1. "Bottoms" refers to the distillation residue stream 23 of FIG. 1. Asterisk ("*") indicates that the weight-percent value was below 0.01.

As shown in Table 11 above, the 1,3-dichloro-2-propanol overheads rate is 30.01 weight-percent of the 0.33 kg/hr overheads rate or 0.10 kg/hr and the 2,3-dichloro-1-propanol rate is 1.42 weight-percent of the 0.33 kg/hr overheads rate or 0.005 kg/hr. The sum of the 1,3-dichloro-2-propanol feed rate (0.10 kg/hr) and 2,3-dichloro-1-propanol feed rate (0.005 kg/hr), is 0.10 kg/hr.

DCH recovery of the first distillation is therefore 10.0 percent of the DCH in the feed (0.10÷1.05×100).

The DCH bottoms rate of the first distillation may be calculated by the same method above. In Table 11 above, the 1,3-dichloro-2-propanol bottoms rate is 35.30 weight-percent of the 2.27 kg/hr bottoms rate or 0.80 kg/hr and the 2,3-dichloro-1-propanol rate is 5.6 weight-percent of the 2.27 kg/hr bottoms rate or 0.13 kg/hr. The DCH bottoms rate of the first distillation is the sum of the 1,3-dichloro-2-propanol bottoms rate (0.80 kg/hr) and 2,3-dichloro-1-propanol bottoms rate (0.13 kg/hr), is 0.93 kg/hr.

To model the two column in series arrangement, similar to that of Example 1, feed composition for the second distillation column in Example 3 is made to have similar composition as to the first distillation residue of Example 3, referred to as the "bottoms" in Table 11. The second column pressure of Example 3 is also kept at 1.2 kPa, as shown in Table 10, similar to the second column pressure of Example 1. The data and results are shown below in Table 12.

TABLE 12

| Subject | Feed | Overheads | Bottoms | Units |
|---|---|---|---|---|
| Rate | 2.14 | 0.90 | 1.15 | kg/hr |
| HCl | 0.2 | 0.1 | * | |
| $H_2O$ | 1.4 | 3.7 | 0.1 | |
| 1,3-dichloro-2-propanol | 36.8 | 82.5 | 0.2 | wt. % |
| 2,3-dichloro-1-propanol | 6.7 | 12.9 | 0.5 | wt. % |
| 3-chloro-1,2-propanediol | 15.2 | * | 30.5 | wt. % |
| 2-chloro-1,3-propanediol | 15.6 | * | 25.1 | wt. % |
| glycerin | 9.2 | * | 12.3 | wt. % |

From the above data in Table 12, the DCH overheads rate may be calculated by adding the weight-percent values for 1,3-dichloro-2-propanol (82.5 wt. %) and 2,3-dichloro-1-propanol (12.9 wt. %), dividing the sum by 100, and multiplying the resulting value with the 0.90 kg/hr overheads rate to obtain 0.86 kg/hr.

The DCH feed rate to the second distillation equals to the bottoms rate of the first distillation (0.93 kg/hr). DCH recovery from the second column is therefore 92.4 percent (0.86 0.93×100).

The total DCH overheads rate from the first distillation column (0.10 kg/hr) and from the second distillation column (0.86 kg/hr) is then 0.96 kg/hr (0.10 +0.86).

The total DCH recovery obtained with the first distillation combined with the second distillation column is then 91.4 percent (0.96÷1.05×100), which is 13.0% better than the total DCH recovery obtained from the Comparative Example A(78.4%).

As can be seen from the foregoing Example 3 results support the computer simulation results shown in Example 1.

The DCH recovery obtained in Example 3 is higher than that of Example 1 wherein is mostly due to the distillation columns in Example 3 being operated at higher temperatures.

What is claimed is:

1. A process for recovering dichlorohydrin(s) from a mixture comprising dichlorohydrin(s), one or more compounds comprising ester(s) of chlorohydrin(s), monochlorohydrin(s), and/or multihydroxylated-aliphatic hydrocarbon compound(s) and/or ester(s) thereof; water at a concentration of less than 43 weight percent; and optionally one or more substances comprising, chlorinating agent(s), catalyst(s), ester(s) of catalyst(s), and/or heavy byproduct(s), wherein the process comprises:

(a) providing a vapor or liquid phase mixture comprising dichlorohydrin(s), one or more compounds comprising ester(s) of chlorohydrin(s), monochlorohydrin(s), and/or multihydroxylated-aliphatic hydrocarbon compound(s) and/or ester(s) thereof; water at a concentration of less than 43 weight percent; and optionally one or more substances comprising, chlorinating agent(s), catalyst(s), ester(s) of catalyst(s), and/or heavy byproduct(s);

(b) distilling or fractionating the mixture of step (a) in one or more unit operations to separate a lower boiling fraction comprising dichlorohydrin(s) and other compounds having a lower boiling point than the dichlorohydrin(s) present in the mixture from the mixture of step (a) to form a higher boiling fraction comprising the residue of the distillation or fractionation of this step (b);

(c) distilling or fractionating the higher boiling fraction produced by step (b) to separate dichlorohydrin(s) from the higher boiling fraction components present in the mixture from the mixture of step (b) to form an even higher boiling fraction comprising the residue of the distillation or fractionation of this step (c) and to form a vapor fraction comprising dichlorohydrin(s);

(d) recovering at least a portion of the lower boiling fraction produced by step (b) and at least a portion of the vapor fraction produced by step (c);

(e) combining the lower boiling fraction produced by step (b) with the vapor fraction produced by step (c) without prior distillation or fractionation of the vapor fraction produced by step (c);

(f) recovering dichlorohydrin(s) from the lower boiling fraction produced by step (b) and/or the vapor fraction produced by step (d); and (g) recycling at least a portion of the even higher boiling fraction produced by step (c) to the hydrochlorination step.

2. The process according to claim 1, wherein at least one of the chlorinating agent(s) is present in the mixture provided in step (a); wherein the at least one chlorinating agent(s) comprises hydrogen chloride; and including further the step of removing at least 50 percent of the at least one chlorinating agent(s) present in mixture (a) from the mixture (a) prior to step (c).

3. The process according to claim 1, (i) wherein 10 to 95 percent of the total amount of dichlorohydrin(s) in the mixture provided in step (a) is present in the lower boiling fraction produced by step (b); (ii) wherein steps (b) or (c) are carried out at a pressure in the range from 0.1 kPa to 0.2 MPa, and wherein the temperature of the higher boiling fraction during steps (b) or (c) is in the range from 50° C. to 169° C.; or (iii) wherein at least one of the monochlorohydrin(s) and/or ester(s) thereof is present in the mixture provided in step (a), wherein at least one of the monochlorohydrin(s) and/or ester(s) thereof is present in the higher boiling fraction produced by step (b), wherein at least one of the multihydroxylated-aliphatic hydrocarbon compound(s) and/or ester(s) thereof is present in the mixture provided in step (a), and wherein at least one of the multihydroxylated-aliphatic hydrocarbon compound(s) and/or ester(s) thereof is present in the higher boiling fraction produced by step (b).

4. The process according to claim 1, wherein at least one of the catalyst(s) is present in the mixture provided in step (a) comprises a catalyst for hydrochlorinating monochlorohydrin(s) and/or ester(s) thereof and/or for hydrochlorinating multihydroxylated-aliphatic hydrocarbon compound(s) and/or ester(s) thereof; and (1) wherein the catalyst is at least one carboxylic acid, at east one ester of at least one carboxylic acid, or a combination thereof, and wherein the catalyst has a boiling point greater than the boiling point of the highest boiling dichlorohydrin in step (b); or (2) wherein the catalyst (i) is a carboxylate derivative having from two to 20 carbon atoms and containing at least one functional group selected from the group consisting of an amine, an alcohol, a halogen, a sulfhydryl, an ether, an ester, and a combination thereof, and wherein the functional group is attached no closer to the acid function than the alpha carbon; (ii) is less volatile than the dichlorohydrin(s); and (iii) contains heteroatom substituents.

5. The process according to claim 1, including further the step of epoxidizing the dichlorohydrin(s) present in the lower boiling fraction and vapor fraction recovered in step (d) to form epichlorohydrin without additional purification of the dichlorohydrin(s) other than optionally via the liquid-liquid phase separation or optionally via distillation or fractionation.

6. The process according to claim 1, (i) wherein the mixture provided in step (a) is produced or derived from hydrochlorination of monochlorohydrin(s) and/or ester(s) thereof and/or multi hydroxylated-aliphatic hydrocarbon compound(s) and/or ester(s) thereof in the presence of a chlorinating agent; (ii) wherein the hydrochlorination step is carried out in a liquid phase at a temperature below the boiling point of the lowest boiling chlorohydrin in the mixture of step (a), and the mixture provided in step (a) comprises at least a portion of a liquid phase effluent of the hydrochlorination step; (iii) wherein the chlorinating agent is hydrogen chloride, and wherein the hydrochlorination step is carried out using a source of a superatmospheric partial pressure of hydrogen chloride as the chlorinating agent; and (iv) wherein at least a portion of the hydrogen chloride is removed from the liquid phase effluent prior to step (b) via a reduction in pressure permitting escape of hydrogen chloride dissolved in the liquid phase effluent, and wherein less than 1 percent dichlorohydrin is removed from the liquid phase effluent prior to step (b).

7. The process according to claim 1, wherein all of the steps (a)-(g) of the process are carried out simultaneously and continuously for a predetermined period of time.

8. The process according to claim 6, wherein at least 95 percent of the dichlorohydrin(s) produced during hydrochlorination step is recovered in step (d).

9. An apparatus for producing dichlorohydrin(s) from multihydroxylated-aliphatic hydrocarbon compound(s) and/or ester(s) thereof comprising:
(1) at least one reactor;
(2) at least one first separation device comprising at least one first liquid-vapor contacting device having a bottom end and a top end; said first liquid-vapor contacting device including a means for applying a gradually decreasing temperature gradient from the bottom end to the top end to substances within the first liquid-vapor contacting device; and
(3) at least one second separation device comprising at least one second liquid-vapor contacting device having a bottom end and a top end; said second liquid-vapor contacting device including a means for applying a gradually decreasing temperature gradient from the bottom end to the top end to substances within the second liquid-vapor contacting device;
(i) a means for connecting the at least one reactor (10) directly or indirectly to the at least one first separation device (20); and a means for conducting a reactor effluent feed stream (13) from the at least one reactor (10) to the at least one first separation device (20); wherein the first separation device is adapted for distilling and/or fractionating the reactor effluent feed stream; wherein the reactor effluent feed stream is a liquid phase mixture comprising dichlorohydrin(s), one or more compounds comprising ester(s) of chlorohydrin(s), monochlorohdrin(s), and/or multihydroxylated-aliphatic hydrocarbon compound(s) and/or ester(s) thereof: water at a concentration of less than 43 weight percent; and
optionally one or more substances comprising, chlorinating agent(s), catalyst(s), ester(s) of catalyst(s), and/or heavy byproduct(s);
(ii) a means for connecting the at least one first separation device (20) directly or indirectly to the at least one second separation device (30); and a means for conducting a distilled or fractionated liquid residue feed stream (23) from the at least one first separation device (20) to the at least one second separation device (30); wherein the second separation device is adapted for further distilling and/or fractionating the distilled or fractionated liquid residue feed stream from the at least one first separation device;
(iii) wherein the at least one first separation device (20) has a first port (22); and a means for recovering a dichlorohydrin(s)-containing distillate from the at least one first separation device (20);
(iv) wherein the at least one second separation device (30) is connected directly or indirectly to the at least one reactor (10); and for a means for conducting and recycling the liquid residue from the at least one second separation device (30) to the at least one reactor (10);
(v) wherein the at least one second separation device (30) has at least one second port (31); and a means for recovering a dichlorohydrin(s)-containing distillate from the at least one second separation device (30);
(vi) wherein the at least one second separation device (30) further comprises a means for purging and removing heavy byproducts from the liquid residue recycled from the at least one second separation device (30) to the at least one reactor (10);
(vii) wherein at least one second separation device (30) further comprises a venting means for venting a gas stream (35) from the at least one second separation device (30); a means for applying a vacuum to the at least one second separation device (30); and a means for reducing the pressure in the at least one second separation device (30) below ambient atmospheric pressure;
(viii) wherein the at least one first separation device (20) further comprises a means for venting and removing gases at the top of the at least one first separation device (20); and
(ix) wherein the at least one first separation device (20) and/or the at least one second separation device (30) comprise columns and the columns are distillation columns.

10. The apparatus according to claim 9, including further at least one flash vessel; a means for connecting the at least one reactor (10) to the at least one flash vessel, a means for conducting a reactor effluent feed stream (13) from the at least one reactor (10) as a liquid-phase feed stream to the at least one flash vessel, whereby the liquid-phase feed stream conducted from the reactor (10) to the at least one flash vessel is separated into a vapor phase and a liquid phase in the flash vessel; a means for reducing the pressure on the liquid phase; a means for introducing the separated liquid phase into the first separation device (20) for distillation or fractionation; a recycle conduit means (33) for connecting the at least one second separation device (30) to the at least one reactor (10); and a means for conducting a recycle feed stream comprising a distillation- and/or fractionation residue from the at least one second separation device (30) to the at least one reactor (10).

11. An apparatus for producing dichlorohydrin(s) from multihydroxylated-aliphatic hydrocarbon compound(s) and/or ester(s) thereof comprising:
(1) at least one reactor;
(2) at least one first separation device comprising at least one first liquid-vapor contacting device having a bottom end and a top end; said first liquid-vapor contacting device including a means for applying a gradually decreasing temperature gradient from the bottom end to the top end of the at least one first liquid-vapor contacting device to substances within the at least one first liquid-vapor contacting device; and
(3) at least one second separating device comprising at least one second liquid-vapor contacting device having a bottom end and a top end; said second liquid-vapor contacting device including a means for applying a gradually decreasing temperature gradient from the bottom end to the top end of the at least one second liquid-vapor contacting device to substances within the at least one second liquid-vapor contacting device, a means for introducing a vapor stream (53) leaving the at least one first separation device (50) to the at least one second separation device (60) in the upper portion of the second separation device (60), a means for returning a portion of a liquid flow (69) from a lower portion of the at least one second separation device (60) to the at least one first separation device (50), whereby a condenser is eliminated from the at least one first separation device (50);

a means for introducing a liquid stream (52) leaving the bottom end of the first separation device (50) to the second separation device (60) in the lower portion of the second separation device (60); a means for extracting effluent streams of the at least one second separation device (60) from at least five locations on the second separation device (60);

a means for applying a vacuum to the at least one second separation device (60); and a means for reducing the pressure in the at least one second separation device (60) below ambient atmospheric pressure; and wherein the at least five locations on the second separation device (60) include:

(i) a means for removing gases from the top of the at least one second separation device (60);

(ii) a means for removing gases from above where the vapor stream (53) from the at least one first separation device (50) enters the second separation device (60), (iii) a means for removing gases from the bottom end of the second separation device (60) above where the liquid stream (52) from the first separation device (50) enters the second separation device (60), (iv) a means for removing gases from the second separation device (60) in between the entering locations of the feed streams from the first separation device (50) to the second separation device (60);

(v) a means for removing gases as at least one residue stream (64) from the bottom of the second separation device (60) and for recycling the at least one residue stream (64) from the second separation device (60) to the at least one reactor (10); and a purge means (66) for removing heavy byproducts from the at least one residue stream (64); and wherein the at least one first separation device (50) and the at least one second separation device (60) comprise columns and the columns are distillation columns.

12. The apparatus according to claim 11, including further at least one flash vessel; a means for connecting the at least one reactor (10) to the at least one flash vessel, a means for conducting a reactor effluent feed stream (13) from the at least one reactor (10) as a liquid-phase feed stream to the at least one flash vessel, whereby the liquid phase feed stream conducted from the reactor (10) to the at least one flash vessel is separated into a vapor phase and a liquid phase in the flash vessel; a means for reducing the pressure on the liquid phase; a means for introducing the separated liquid phase into the first separation device (50) for distillation or fractionation; a recycle conduit means (64) for connecting the at least one second separation device (60) to the at least one reactor (10); and a means for conducting a recycle feed stream comprising a distillation- and/or fractionation residue from the at least one second separation device (60) to the at least one reactor (10).

13. The apparatus according to claim 9 or 11, including further a liquid-liquid phase separator; a means for connecting the separator, directly or via a cooling device, to a reflux zone of the distillation column(s); a means for separating a condensed liquid aqueous phase from a condensed liquid organic phase in the separator; and a means for conducting the liquid aqueous phase from the liquid-liquid phase separator to the reflux zone of the distillation column(s).

14. The apparatus according to claim 9 or claim 11, including further one or more distillation columns, extraction columns, absorption columns, reboilers, and condensers, and combinations thereof, and a means for connecting the one or more distillation columns, extraction columns, absorption columns, reboilers, and condensers, and combinations thereof to the at least one reactor (10), the at least one column (20), and/or the at least one column (50).

15. The apparatus according to claim 9 or 11, including further an absorption system means for absorbing a vent gas leaving the reactor (10); wherein an absorbent liquid is used in the absorption system means; and wherein the absorbent liquid is selected from the group consisting of multihydroxylated aliphatic hydrocarbons, esters of multihydroxylated aliphatic hydrocarbons, organic acid catalysts, at least a portion of the recycle stream from the second separation device (30), or at least a portion of the recycle stream from the second separation device (60).

16. The apparatus according to claim 9 or claim 11, including further a reboiler means; a means for connecting the reboiler means to the at least one first separation device (20) or to the at least one first separation device (50); and a means for heating the feed stream(s) conducted to the at least one first liquid-vapor contacting device of the at least one separation device (20) or of the at least one separation device (50).

* * * * *